United States Patent
Ogle et al.

(10) Patent No.: US 9,937,255 B2
(45) Date of Patent: Apr. 10, 2018

(54) COATED BALLOONS FOR BLOOD VESSEL STABILIZATION

(75) Inventors: Matthew F. Ogle, Fitchburg, WI (US); Wenda C. Carlyle, Prairie Farm, WI (US); Edward J. Anderson, Maple Grove, MN (US); Kishore Udipi, Santa Rosa, CA (US)

(73) Assignee: NECTERO MEDICAL, INC., Dover, DE (US)

( * ) Notice: Subject to any disclaimer, the term of this patent is extended or adjusted under 35 U.S.C. 154(b) by 536 days.

(21) Appl. No.: 13/474,342

(22) Filed: May 17, 2012

(65) Prior Publication Data
US 2012/0323211 A1 Dec. 20, 2012

Related U.S. Application Data

(60) Provisional application No. 61/487,541, filed on May 18, 2011.

(51) Int. Cl.
*A61L 29/08* (2006.01)
*A61K 47/32* (2006.01)
(Continued)

(52) U.S. Cl.
CPC .............. *A61K 47/32* (2013.01); *A61K 31/11* (2013.01); *A61K 31/7024* (2013.01);
(Continued)

(58) Field of Classification Search
None
See application file for complete search history.

(56) References Cited

U.S. PATENT DOCUMENTS 2,987,446 A    6/1961   Riethmuller
4,992,264 A    2/1991   Diot et al.
(Continued)

FOREIGN PATENT DOCUMENTS

EP    0617964 A1    10/1994
GB    2057437 A     4/1981
(Continued)

OTHER PUBLICATIONS

European Search Report and Opinion from copending application No. 12785593.0 dated Oct. 22, 2014 (8 pages).
(Continued)

*Primary Examiner* — Brian Gulledge
(74) *Attorney, Agent, or Firm* — Knobbe Martens Olson & Bear LLP

(57) ABSTRACT

A coated balloon device for stabilizing a section of a blood vessel in a living subject is disclosed. The coating layer of the coated balloon comprises a phenolic compound having a plurality of phenolic groups connected to form a hydrophobic core with peripheral phenolic hydroxyl groups. The coating layer of the coated balloon may contain a hydrophilic polymer to facilitate the release of the phenolic compound. The balloon in general is made of a compliant polymer for atraumatic contact with the blood vessel. In some embodiments, the coating of the coated balloon device further comprises a hydrophilic undercoat layer between the balloon and the coating layer. In some embodiments, the coated balloon device further comprises a sacrificial top coating that dissolves upon delivery into the section of the blood vessel and comprises a hydrophilic composition including sugar, sugar derivatives, or a combination thereof.

30 Claims, 11 Drawing Sheets

(51) Int. Cl.
*A61K 31/11* (2006.01)
*A61K 31/7024* (2006.01)
*A61L 29/06* (2006.01)
*A61L 29/14* (2006.01)
*A61L 29/16* (2006.01)
*A61M 25/10* (2013.01)

(52) U.S. Cl.
CPC .............. *A61L 29/06* (2013.01); *A61L 29/085* (2013.01); *A61L 29/145* (2013.01); *A61L 29/16* (2013.01); *A61L 2300/102* (2013.01); *A61M 25/104* (2013.01); *A61M 25/1011* (2013.01); *A61M 2025/105* (2013.01); *A61M 2025/1052* (2013.01); *A61M 2025/1075* (2013.01); *A61M 2025/1086* (2013.01); *A61M 2025/1097* (2013.01); *F04C 2270/0421* (2013.01)

(56) References Cited

U.S. PATENT DOCUMENTS

| | | |
|---|---|---|
| 5,015,677 A | 5/1991 | Benedict et al. |
| 5,019,400 A | 5/1991 | Gombotz et al. |
| 5,081,157 A | 1/1992 | Pomerantz |
| 5,102,402 A | 4/1992 | Dror et al. |
| 5,252,344 A | 10/1993 | Shi |
| 5,269,770 A | 12/1993 | Conway et al. |
| 5,304,121 A | 4/1994 | Sahatjian |
| 5,512,291 A | 4/1996 | Li |
| 5,700,287 A | 12/1997 | Myers et al. |
| 5,720,950 A | 2/1998 | Poiani et al. |
| 5,750,150 A | 5/1998 | Okazaki et al. |
| 5,834,449 A | 11/1998 | Thompson et al. |
| 5,876,744 A | 3/1999 | Della Valle et al. |
| 5,916,597 A | 6/1999 | Lee et al. |
| 5,922,253 A | 7/1999 | Herbert et al. |
| 5,955,097 A | 9/1999 | Tapolsky et al. |
| 5,968,500 A | 10/1999 | Robinson |
| 5,972,999 A | 10/1999 | Murad |
| 6,063,770 A | 5/2000 | Falcon |
| 6,071,541 A | 6/2000 | Murad |
| 6,107,453 A | 8/2000 | Zuccato et al. |
| 6,146,616 A | 11/2000 | Msika et al. |
| 6,228,387 B1 | 5/2001 | Borod |
| 6,235,294 B1 | 5/2001 | Perrier et al. |
| 6,239,114 B1 | 5/2001 | Guthrie et al. |
| 6,254,898 B1 | 7/2001 | Bragaglia |
| 6,258,122 B1 | 7/2001 | Tweden et al. |
| 6,290,949 B1 | 9/2001 | French et al. |
| 6,293,923 B1 | 9/2001 | Yachia et al. |
| 6,432,922 B1 | 8/2002 | Brunck et al. |
| 6,437,004 B1 | 8/2002 | Perricone |
| 6,444,234 B1 | 9/2002 | Kirby et al. |
| 6,463,317 B1 | 10/2002 | Kucharczyk et al. |
| 6,469,053 B1 | 10/2002 | Romanczyk, Jr. et al. |
| 6,471,723 B1 | 10/2002 | Ashworth et al. |
| 6,471,973 B1 | 10/2002 | Perrier et al. |
| 6,517,824 B1 | 2/2003 | Kohn et al. |
| 6,531,154 B1 | 3/2003 | Mathiowitz et al. |
| 6,576,613 B1 | 6/2003 | Brunck et al. |
| 6,586,405 B2 | 7/2003 | Semple et al. |
| 6,610,320 B2 | 8/2003 | Schmitz et al. |
| 6,630,163 B1 | 10/2003 | Murad |
| 6,676,977 B2 | 1/2004 | Murad |
| 6,747,059 B1 | 6/2004 | Romanczyk, Jr. et al. |
| 6,773,704 B1 | 8/2004 | Chapman et al. |
| 6,787,152 B2 | 9/2004 | Kirby et al. |
| 6,793,664 B2 | 9/2004 | Mazzocchi et al. |
| 6,800,292 B1 | 10/2004 | Murad |
| 6,830,577 B2 | 12/2004 | Nash et al. |
| 6,847,848 B2 | 1/2005 | Sterzer et al. |
| 6,867,188 B2 | 3/2005 | Qvist et al. |
| 6,927,205 B2 | 8/2005 | Patt |
| 6,927,206 B2 | 8/2005 | Patt |
| 6,929,626 B2 | 8/2005 | DiCarlo et al. |
| 6,979,347 B1 | 12/2005 | Wu et al. |
| 6,986,868 B2 | 1/2006 | Madsen |
| 7,008,411 B1 | 3/2006 | Mandrusov et al. |
| 7,060,051 B2 | 6/2006 | Palasis |
| 7,150,853 B2 | 12/2006 | Lee et al. |
| 7,182,744 B2 | 2/2007 | Yamasaki et al. |
| 7,208,179 B1 | 4/2007 | Drohan et al. |
| 7,252,834 B2 | 8/2007 | Vyavahare et al. |
| 7,252,934 B2 | 8/2007 | Boersma et al. |
| 7,314,480 B2 | 1/2008 | Eidenschink et al. |
| 7,323,169 B2 | 1/2008 | Goldenberg et al. |
| 7,371,257 B2 | 5/2008 | Sahatjian et al. |
| 7,491,188 B2 | 2/2009 | Holman et al. |
| 7,658,966 B2 | 2/2010 | Kokish |
| 7,695,674 B2 | 4/2010 | Varma et al. |
| 7,713,543 B2 | 5/2010 | Vyavahare et al. |
| 7,794,775 B2 | 9/2010 | Stratford et al. |
| 7,879,270 B2 | 2/2011 | Varma et al. |
| 8,052,668 B2 | 11/2011 | Sih |
| 8,100,961 B2 | 1/2012 | Vyavahare et al. |
| 2001/0029349 A1 | 10/2001 | Leschinsky |
| 2003/0027863 A1 | 2/2003 | Cruz et al. |
| 2003/0078659 A1 | 4/2003 | Yang |
| 2003/0170287 A1 | 9/2003 | Prescott |
| 2003/0171287 A1 | 9/2003 | Morishita et al. |
| 2003/0228364 A1 | 12/2003 | Nathan |
| 2003/0232895 A1 | 12/2003 | Omidian et al. |
| 2004/0044404 A1 | 3/2004 | Stucke et al. |
| 2004/0148016 A1 | 7/2004 | Klein et al. |
| 2004/0153145 A1 | 8/2004 | Simionescu et al. |
| 2004/0158320 A1 | 8/2004 | Simionescu et al. |
| 2004/0181252 A1 | 9/2004 | Boyle et al. |
| 2004/0213933 A1 | 10/2004 | Varma |
| 2005/0064011 A1 | 3/2005 | Song et al. |
| 2005/0079202 A1 | 4/2005 | Chen et al. |
| 2005/0245893 A1 | 11/2005 | Leschinsky |
| 2006/0034925 A1 | 2/2006 | Au et al. |
| 2006/0240066 A1 | 10/2006 | Vyavahare et al. |
| 2007/0128242 A1 | 6/2007 | Zhao |
| 2007/0142772 A1 | 6/2007 | Deshmukh et al. |
| 2007/0212386 A1 | 9/2007 | Patravale et al. |
| 2007/0212387 A1* | 9/2007 | Patravale et al. ............ 424/422 |
| 2007/0282422 A1* | 12/2007 | Biggs et al. ................. 623/1.13 |
| 2007/0293937 A1 | 12/2007 | Biggs et al. |
| 2008/0255508 A1 | 10/2008 | Wang |
| 2008/0255510 A1 | 10/2008 | Wang |
| 2009/0069883 A1 | 3/2009 | Ding et al. |
| 2009/0105686 A1 | 4/2009 | Snow et al. |
| 2009/0140449 A1 | 6/2009 | Varma et al. |
| 2009/0155337 A1* | 6/2009 | Schreck et al. ............... 424/426 |
| 2009/0186370 A1 | 7/2009 | Ogle et al. |
| 2009/0214654 A1 | 8/2009 | Isenburg et al. |
| 2009/0227980 A1 | 9/2009 | Kongas et al. |
| 2009/0258049 A1 | 10/2009 | Klein et al. |
| 2010/0016833 A1 | 1/2010 | Ogle et al. |
| 2010/0119605 A1 | 5/2010 | Isenburg et al. |
| 2010/0189876 A1 | 7/2010 | Kokish et al. |
| 2010/0209472 A1 | 8/2010 | Wang |
| 2010/0292641 A1 | 11/2010 | Wijay et al. |
| 2010/0318029 A1* | 12/2010 | Pepper et al. ........... 604/103.07 |
| 2011/0093000 A1* | 4/2011 | Ogle et al. .................... 606/194 |
| 2011/0218517 A1 | 9/2011 | Ogle et al. |
| 2012/0015019 A1 | 1/2012 | Pacetti et al. |
| 2012/0197284 A1 | 8/2012 | Ogle et al. |

FOREIGN PATENT DOCUMENTS

| | | |
|---|---|---|
| JP | H09-500561 A | 1/1997 |
| JP | 10-130155 | 5/1998 |
| WO | 95-03083 A1 | 2/1995 |
| WO | 01/21228 A1 | 3/2001 |
| WO | 01/41735 A2 | 6/2001 |
| WO | 2004/047620 A2 | 6/2004 |
| WO | 2007/064152 A1 | 6/2007 |
| WO | 2007/133479 A2 | 11/2007 |
| WO | 2009/036118 A1 | 3/2009 |
| WO | 2009/061787 A1 | 5/2009 |
| WO | 2010/026578 A1 | 3/2010 |

(56) References Cited

FOREIGN PATENT DOCUMENTS

| WO | 2010/027735 | A2 | 3/2010 |
| WO | 2010/080575 | A2 | 7/2010 |
| WO | 2010/120620 | A1 | 10/2010 |
| WO | 2010/140163 | A2 | 12/2010 |
| WO | 2011/044455 | | 4/2011 |

OTHER PUBLICATIONS

Ammoury et al., "Jejunal absorption, pharmacological activity, and pharmacokinetic evaluation of indomethacin-loaded poly(d,l-lactide) and poly(isobutyl-cyanoacrylate) nanocapsules in rats," Pharm. Res., 8(1):101-105 (1991) (abstract only).

BASF Corporation, Pluronic(R) F127 Block Copolymer Surfactant Technical Bulletin, 2002 (1 page).

Blonder et al., "Dose-Dependent Hyperlipidemia in Rabbits Following Administration of Poloxamer 407 Gel," Life Sciences, 65(21):PL 261-266 (1999).

Brem et al., "Interstitial chemotherapy with drug polymer implants for the treatment of recurrent gliomas," J. Neurosurgery, 74(3):441-446 (1991).

Bu et al., "IKKβ-dependent NF-κB pathway controls vascular inflammation and intimal hyperplasia," The FASEB Journal express article 10.1096/fj.04-2645fje., published online Jun. 6, 2005 (18 pages).

Calvo et al., "Long-circulating PEGylated polycyanoacrylate nanoparticles as new drug carrier for brain delivery," Pharm. Res., 18(8):1157-1166 (2001).

Choke et al., "A Review of Biological Factors Implicated in Abdominal Aortic Aneurysm Rupture," Eur. J. Vasc. Endovasc. Surg., 30(3):227-244 (2005).

Connolly et al., "Triglycidylamine crosslinking of porcine aortic valve cusps or bovine pericardium results in improved biocompatibility, biomechanics and calcification resistance," Am. J. Pathol., 166(1):1-13 (2005).

Daugherty et al., "Mouse models of abdominal aortic aneurysms," Arterioscler. Throat. Vasc. Biol., 24 (3):429-434 (2004).

Dawson et al., "Pharmacotherapy of abdominal aortic aneurysms," Curr. Vasc. Pharmacol., 4(2):129-149 (2006).

Freestone et al., "Influence of Hypercholesterolemia and Adventitial Inflammation on the Development of Aortic Aneurysm in Rabbits," Arterioscler. Thromb. Vasc. Biol., 17:10-17 (1997).

Freestone et al., "Inflammation and Matrix Metalloproteinases in the Enlarging Abdominal Aortic Aneurysm," Arterioscler. Thromb. Vasc. Biol., 15:1145-1151 (1995).

Gertz et al., "Aneurysm of the rabbit common carotid artery induced by periarterial application of calcium chloride in vivo," J. Clin. Invest., 81:649-656 (1988).

Harvard Health Publications, "Hemorrhoids and what to do about them," http://www.revolutionhealth.com/conditions/digestive/hemorrhoids/introduction/what-to-do, Aug. 21, 2006 (5 pages).

Isenburg et al., "Elastin stabilization for treatment of abdominal aortic aneurysms," Circulation, 115 (13):1729-1737 (2007).

Isenburg et al., "Structural requirements for stabilization of vascular elastin by polyphenolic tannins," Biomaterials, 27:3645-3651 (2006).

Isenburg et al., "Tannic acid treatment enhances biostability and reduces calcification of glutaraldehyde fixed aortic wall," Biomaterials, 26:1237-1245 (2005).

Isenburg et al., "Elastin stabilization in cardiovascular implants: Improved resistance to enzymatic degredation by treatment with tannic acid," Biomaterials, 25:3293-3302 (2004).

Jayakrishnan et al., "Glutaraldehyde as a fixative in bioprostheses and drug delivery matrices," Biomaterials, 17 (5):471-484 (1996).

Jorge-Herrero et al., "Calcification of pericardial tissue pretreated with different amino acids," Biomaterials 17 (6):571-575 (1996).

Kasyanov et al., "Tannic acid mimicking dendrimers as small intestine submucosa stabilizing nanomordants," Biomaterials, 27:745-751 (2006).

Kobayashi et al., "Comparison of Elastolytic Activity between Experimental Aneurysm and Experimental Diabetes Mellitus," Biol. Pharm. Bull., 23(7):775-777 (1998).

Luck et al., "Polyphenols, astringency and proline-rich proteins," Phytochemistry, 37(2):357-371 (1994) (abstract only).

Musumeci et al., "PLA/PLGA nanoparticles for sustained release of docetaxel," International Journal of Pharmaceutics, 325:172-179 (2006).

Osakabe et al., "Quantitative Changes of Elastin, Fibrillin and Collagen in Abdominal Aortic Aneurysms," Nippon Ronen Igakkai Zasshi (Japanese Journal of Geriatrics) 37:979-983 (2000) (see English language abstract on p. 983).

Prabha et al., "Critical determinants in PLGA/PLA nanoparticle-mediated gene expression," Pharm Res, 21 (2):354-364 (2004).

Ross et al., "The elastic fiber. I. The separation and partial characterization of its macromolecular components," J. Cell. Biol., 40(2):366-381 (1969).

Simionescu et al., "Lysine-enhanced glutaraldehyde crosslinking of collagenous biomaterials," J. Biomed. Mater. Res., 25(12):1495-1505 (1991) (abstract only).

Simionescu et al., "Galloylglucoses of low molecular weight as mordant in electron microscopy. I. Procedure, and evidence for mordanting effect," J. Cell. Biol., 70(3):608-621 (1976).

Stacchino et al. "Detoxification process for glutaraldehyde-treated bovine pericardium: biological, chemical and mechanical characterization," J. Heart Valve Dis., 7(2):190-4 (1998) (abstract only).

Tambiah et al., "Provocation of Experimental Aortic Inflammation and Dilatation by Inflammatory Mediators and Chlamydia Pneumoniae," British Journal of Surgery, 88:935-940 (2001).

Vyavahare et al., "Elastin calcification and its prevention with aluminum chloride pretreatment," Am. J. Pathol., 155(3):973-982 (1999).

Yamaguchi et al., "The Time Course of Elastin Fiber Degeneration in a Rat Aneurysm Model," Surg. Today, 30:727-731 (2000).

International Search Report and Written Opinion from copending PCT application (PCT/US2012/038395) dated Aug. 1, 2012 (10 pages).

Office Action for co-pending Japanese Application No. 2014-51145, dated Mar. 3, 2016 (9 pages).

\* cited by examiner

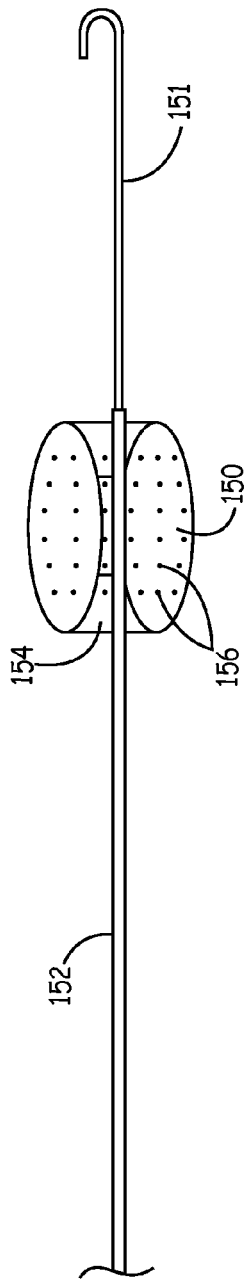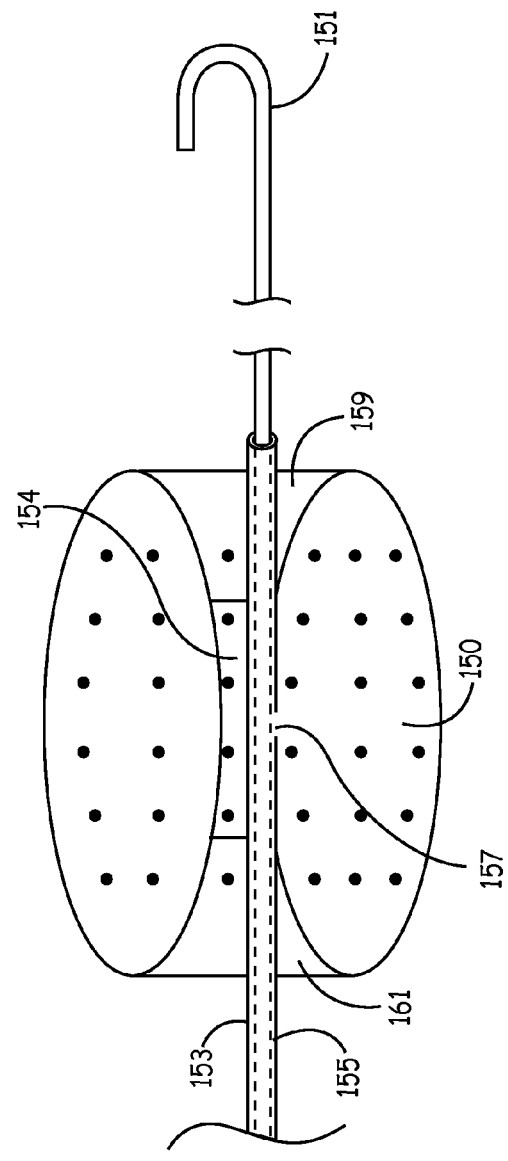

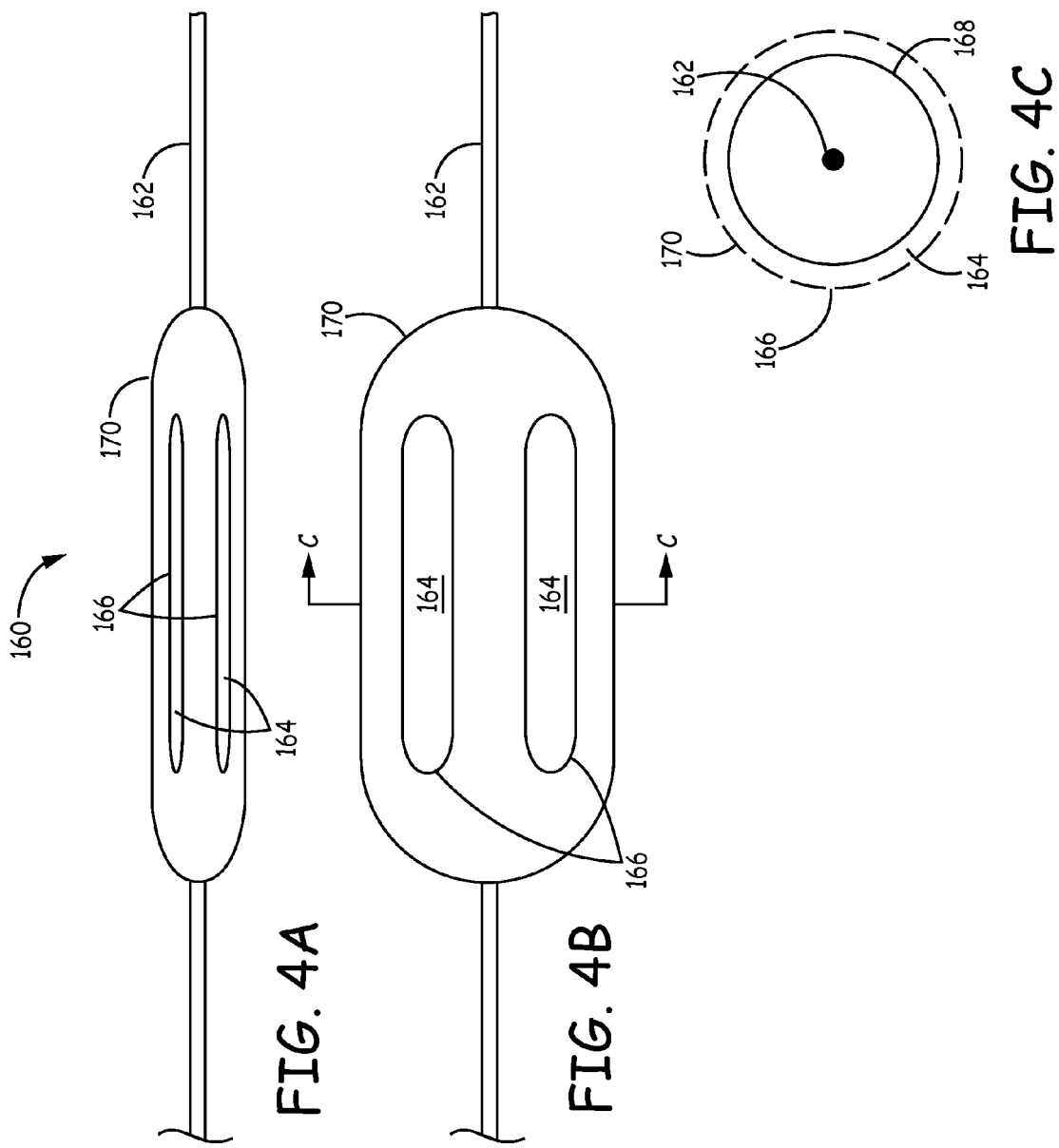

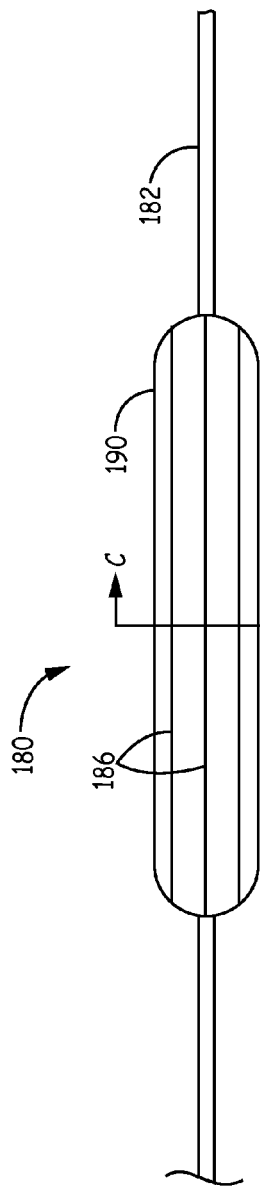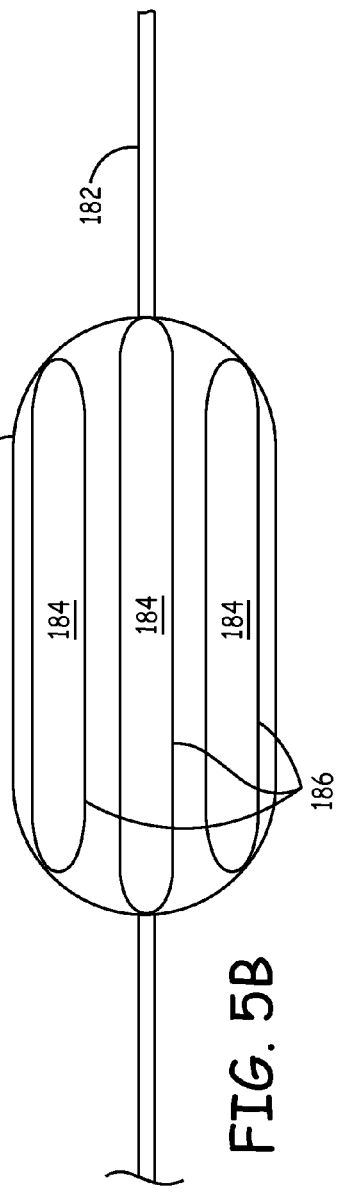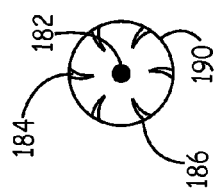

COATED BALLOONS FOR BLOOD VESSEL STABILIZATION

CROSS REFERENCE TO RELATED APPLICATIONS

This application claims priority to U.S. provisional patent application Ser. No. 61/487,541, filed on May 18, 2011 to Ogle et al., entitled "Coated Balloons for Aneurysm Treatment," incorporated herein by reference.

GOVERNMENT RIGHTS

Development of the inventions described herein was at least partially funded with government support through National Institute of Health Grant 1R43 HL103214-1, and the U.S. government has certain rights in the inventions.

FIELD OF THE INVENTION

The inventions, in general, are related to stabilization of blood vessels using coated balloons. The inventions are further related to coated balloons, the formulation of the balloon coating and the formation of the coated balloons.

BACKGROUND

Aneurysms are degenerative diseases characterized by destruction of arterial architecture and subsequent dilatation of the blood vessel that may eventually lead to fatal ruptures. Some common locations for aneurysms include the abdominal aorta (abdominal aortic aneurysm, AAA), thoracic aorta, and brain arteries. In addition, peripheral aneurysms of the leg, namely the popliteal and femoral arteries are prevalent locations of this vascular pathology. The occurrence of such peripheral aneurysms appears to be strongly associated with the presence of aneurysms in other locations, as it has been estimated that 30 to 60% of peripheral aneurysm patients also have an AAA.

Aneurysms can be caused by any of a large class of degenerative diseases and pathologies including atherosclerotic disease, defects in arterial components, genetic susceptibilities, and high blood pressure, among others, and can develop silently over a period of years. The hallmarks of aneurysms include enzymatic degradation of vascular structural proteins such as elastin, inflammatory infiltrates, calcification, and eventual overall destruction of the vascular architecture.

SUMMARY OF THE INVENTION

In a first aspect, the invention pertains to a coated balloon device for stabilizing a section of a blood vessel in a living subject. The coated balloon device comprises a shaft having a proximal end and a distal end, a balloon element comprising an extendable structure having an outer surface, the balloon element being supported by the shaft at or near the distal end of the shaft, and a coating layer associated with the outer surface of the extendable structure. In some embodiments, at least about 5% by weight of the coating layer comprises a therapeutic composition that comprises a phenolic compound having a plurality of phenolic groups connected to form a hydrophobic core with peripheral phenolic hydroxyl groups. The extendable structure of the balloon element comprises an unextended configuration, an inflated but unexpanded configuration, and an expanded configuration.

The therapeutic composition of the coating layer can have little or no unbound gallic acid. In some embodiments, the phenolic compound in the coating layer is tannic acid or an analog of tannic acid, pentagalloylglucose or an analog of pentagalloylglucose, a combination thereof, or a pharmaceutically acceptable salt thereof. In additional embodiments, the phenolic compound of the coating layer is a flavonoid or a flavonoid derivative, a flavolignan or a flavolignan derivative, a phenolic rhizome or a phenolic rhizome derivative, a flavan-3-ol or a flavan-3-ol derivative, a tannin or a tannin derivative, an ellagic acid or an ellagic acid derivative, a procyanidin or a procyanidin derivative, proanthocyanidin, anthocyanins, quercetin, (+)-catechin, (−)-epicatechin, nobotanin, epigallocatechin gallate, gallotannins, hydroxytyrosol (3,4-dihydroxy phenylethanol), oleuropein, prodelphinidin, a combination thereof, or a pharmaceutically acceptable salt thereof. In some embodiments, at least 50% by weight of the coating layer comprises the phenolic compound. In additional or alternative embodiments, the therapeutic composition of the coating layer further comprises glutaraldehyde. In some embodiments, the coating layer of the coated balloon further comprises a hydrophilic natural polymer such as a polysaccharide like dextran, starch, hyaluronic acid as such or as a derivative or a combination thereof or collagen, gelatin, chitin, albumin, alginate, as such or as a derivative or combination thereof or a synthetic polymer including polyvinyl alcohol, polyvinyl pyrrolidone, polyethylene glycol, poly(lactic-co-glycolic acid) as such or as a derivative or a combination thereof. Furthermore, the extendable structure of the balloon element can comprise a compliant polymer and the inflated but unexpanded configuration has a generally cylindrical section along the outer surface. Also, the extendable structure of the balloon element can comprise a low durometer polyurethane balloon material. The shaft of the coated balloon device in some embodiments comprises a balloon lumen having a distal opening into the interior of the balloon element and a proximal connection connected to a fluid source. In some embodiments, the coated balloon device further comprises a by-pass channel with an opening proximal to the balloon element and an opening distal to the balloon element that provides flow past the balloon when expanded in a vessel. In some embodiments, the coating of the coated balloon device further comprises a hydrophilic undercoat layer between the balloon element and the coating layer. The undercoat layer can be optionally crosslinked to the balloon element. In some embodiments, the undercoat layer can be made porous to allow further hydration of the coating layer. In some embodiments, the coated balloon device further comprises a sheath slidably positioned over the shaft having a configuration extended in a distal direction relative to the shaft covering the extendable structure in the unextended configuration. In some embodiments, the coated balloon device further comprises a sacrificial top coating that dissolves upon delivery into the section of the blood vessel and comprises a hydrophilic composition including sugar, sugar derivatives, or a combination thereof.

In another aspect, the invention pertains to a coated balloon device for stabilizing a section of a blood vessel in a living subject that comprises a shaft having a distal end and a proximal end, a balloon element comprising an extendable structure having an outer surface, the balloon element being supported by the shaft at or near the distal end of the shaft, and a coating associated with the outer surface of the extendable structure. The coating can comprise a hydrophilic polymer binder and a therapeutic composition blended with the hydrophilic polymer. The therapeutic composition can comprise a phenolic compound having a plurality of phenolic groups connected to form a hydrophobic core with at least two peripheral phenolic hydroxyl groups. The hydrophilic polymer comprises polyvinyl alcohol, polyvinyl pyrrolidone, polyethylene glycol, poly(lactic-co-glycolic acid), or a combination thereof. In some embodiments, at least 25% by weight of the coating comprises the phenolic compound.

In a further aspect, the invention pertains to a method for stabilizing a section of a blood vessel of a living subject using a coated balloon having a coating that comprises a therapeutic composition that comprises a phenolic compound that binds to the elastin component of the blood vessel to stabilize the blood vessel. The method comprises the steps of deploying the coated balloon at the section of the blood vessel so the coating around a circumference of the balloon is in contact with the blood vessel and keeping the deployed balloon in the blood vessel for a sufficient period of time to allow at least a portion of the therapeutic composition to elute from the coating into the blood vessel to stabilize the blood vessel. The phenolic compound has a plurality of phenolic groups connected to form a hydrophobic core with at least two peripheral phenolic hydroxyl groups. In one embodiment, the method is used to stabilize the section of blood vessel that comprises an aneurysm. After the blood vessel stabilization procedure, the coated balloon is removed from the blood vessel. In additional or alternative embodiments, where the balloon further comprises a sheath, and the method correspondingly further comprises delivering the coated balloon to the section of blood vessel to be stabilized and removing the sheath before deploying the coated balloon. The section of the blood vessel can be treated with glutaraldehyde before or after the stabilization treatment using the coated balloon. Before conducting the blood vessel stabilization procedure, a distal protection device can be deployed to filter the blood flow in the vessel during the procedure.

In an additional aspect, the invention pertains to a method of forming a coated balloon that comprises an extendable structure having an outer surface. The method comprises applying a coating on the outer surface of the extendable structure. The coating comprises a blend of a hydrophilic polymer and a phenolic compound having a plurality of phenolic groups connected to form a hydrophobic core with at least two peripheral phenolic hydroxyl groups. The hydrophilic polymer can comprise, for example, polyvinyl alcohol, polyvinyl pyrrolidone, polyethylene glycol, poly(lactic-co-glycolic acid), or a combination thereof. In some embodiments, the method further comprises applying a hydrophilic undercoat layer on the extendable structure before applying the coating. Prior to applying the hydrophilic undercoat layer, the method may further comprise associating a crosslinking compound to the outer surface of the extendable structure to crosslink with hydrophilic polymer to form the hydrophilic undercoat layer. In some embodiments, the method further comprises applying a sacrificial top coat on the coating of the coated balloon.

BRIEF DESCRIPTION OF THE DRAWINGS

FIG. 3A is a fragmentary side view of a coated balloon device with a by-pass channel and weeping pores on the balloon in an expanded configuration.

FIG. 3B is an enlarged fragmentary, sectional view of the balloon of FIG. 3A.

FIG. 4A is a fragmentary side view of an embodiment of a coated balloon device having a double balloon with slits on the surface of the outer balloon and a coating between the outer balloon and the inner balloon in an inflated but un-expanded configuration.

FIG. 4B is a fragmentary side view of the double balloon device of FIG. 4A in an expanded configuration.

FIG. 4C is a cross sectional view of the double balloon device along the C-C line of FIG. 4B.

FIG. 5A is a fragmentary side view of a coated balloon device with ridges in the balloon in an inflated but unexpanded configuration.

FIG. 5B is a fragmentary side view of the coated balloon device of FIG. 5A in an expanded configuration with the ridges extended exposing the coated therapeutic composition on the surface of the balloon.

FIG. 5C is a cross sectional view of the balloon along the C-C line of FIG. 5A.

DETAILED DESCRIPTION OF PREFERRED EMBODIMENTS

Figure 1:
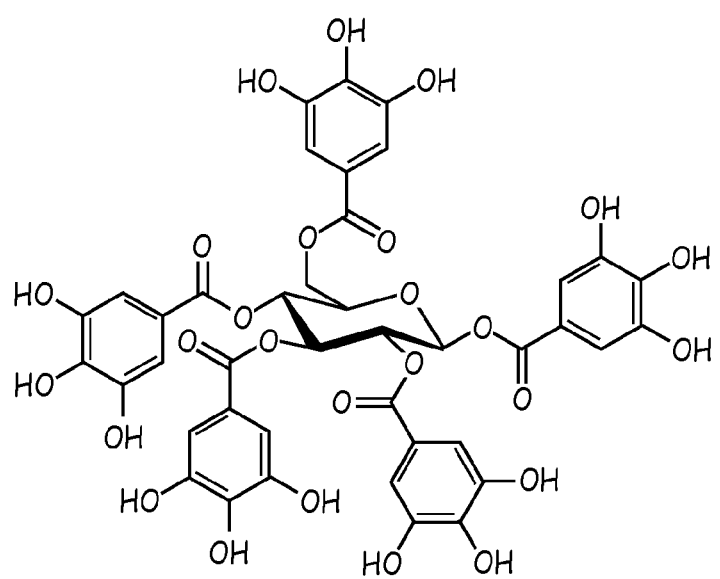
FIG. 1 shows the chemical structure of pentagalloylglucose.

The devices and corresponding processes described herein can provide treatments for blood vessel walls that may be suffering degradation, which may be associated with aneurysm, vulnerable plaque, aortic dissection and/or other conditions. The devices are designed such that procedures can be carried out in a less invasive format that reduces the recovery time and risk of the procedure to the patient. While the device can be used for other procedures, the discussion below focuses on the treatment of an aneurysm since the treatment of aneurysms is an issue of very significant clinical concern.

Coated balloons are described herein for the stabilization of blood vessels such as the treatment of aneurysms and similar vascular degradation. For example, protein stabilization compositions have been identified for the stabilization of aneurysms, and these compositions can be delivered in balloon coatings as described herein, and in some embodiments in coatings for compliant balloons. In particular, polyphenols, which can comprise a hydrophobic molecular core, are of particular interest as elastin stabilization agents. The coating structure can be designed, as described herein, for the rapid delivery of the stabilization agent into the vessel wall. In particular, a suitable coating can be Ruined from a high concentration of the stabilization agent. In further embodiments, the coating can comprise a hydrophilic polymer. Swelling of the hydrophilic polymer following delivery and deployment of the balloon into a patient can facilitate transfer of the elastin stabilization composition into the blood vessel wall. The balloon coatings can be applied to balloons with architectures and compositions that are designed for effective delivery of therapeutic compositions to blood vessels without compromising the vessel integrity. The coated balloons can be designed for effective delivery to the selected location within the blood vessel. The coated balloons in particular can be designed for use in the aorta, which is a location for particularly life threatening AAA events. In some embodiments, the balloon design may provide for perfusion of blood past the balloon and/or for devices to capture any escaped elastin stabilization agents that escape from the delivery location.

Connective tissue generally comprises individual cells not directly attached to one another and held within an extracellular matrix. The extracellular matrix, in turn, comprises compositions excreted by specific cells with specific mechanical properties, which include, for example, fibrous components such as collagen fibers and elastin fibers. Connective tissue can assume widely divergent architectures. Blood vessels generally involve connective tissue, for example, with a thin layer of endothelial cells lining the blood vessel. At an aneurysm, blood vessels exhibit degradation of the connective tissue. Due to the blood pressure in the vessel, as the connective tissue of blood vessel weakens, the vessel generally expands at the location of weakness. The expansion further effects blood flow in the vicinity of the expansion. Upon further weakening of the vessel, the blood vessel can rupture due to the pressure in the vessel with corresponding deleterious effects. The degradation of the connective tissue such as blood vessel can be brought about due to any of a variety of mechanisms and/or conditions including, for example, those associated with aneurysm, atherosclerotic disease, genetic susceptibilities, blunt force injury, Marfan's syndrome, and the like.

Elastin and collagen are protein constituents of connective tissue contributing to the structural integrity of the tissue. Moreover, elastin and collagen are quite abundant in connective tissue. For example, elastin is considered the most abundant extracellular matrix protein found in the aortic wall. Elastin polypeptide chains are naturally cross-linked together to form elastic fibers. Elastin molecules can uncoil into a more extended conformation when the fiber is stretched and will recoil spontaneously as soon as the stretching force is relaxed. Elastin degeneration in connective tissue pathology is generally believed to be caused by enzymes including elastase enzymes and matrix metalloproteinase (MMP) enzymes that can be secreted by vascular cells as well as by infiltrating inflammatory cells.

The characteristics of aneurysms are degeneration of arterial structural proteins including elastin and collagen, inflammatory infiltrates, calcification, and overall degeneration of arterial architecture. This results in loss of mechanical properties and progressive dilatation. Due to its insolubility, natural desmosine and isodesmosine crosslinks, and extremely long biological half-life, elastin is generally perceived to be resistant to degradation. However, there is a specific set of enzymes, matrix metalloproteinases (particularly MMP-2, MMP-9, and MMP-12), which are capable of degrading elastin. MMPs are involved in normal physiological processes such as bone remodeling, wound healing, and angiogenesis. However, abnormally high levels of MMPs have been identified in pathological processes in many vascular diseases, and appear to be significant contributors to the formation and progression of AAAs. This identification is underlined by consistent reports of severe elastin degradation within aneurysmal tissues, as evidenced by heavy degeneration of the arterial architecture, decreased medial elastin content, and disrupted or fragmented elastic lamellae. This degradation is particularly significant when one considers the inability of elastin to promptly revitalize itself (as evidenced by its nearly 70-year biological half-life), unlike some other relatively dynamic matrix components.

Additionally, at an aneurysm, collagen is present throughout the connective tissue. In the course of aneurysm development, it has been suggested that the processes of degradation and regeneration of collagen alternates. Once the collagen degradation reaches a particular degree, the rupture of the aneurysm tissue may occur. See, for example, Choke E, Cockerill G, Wilson W R, et al. *Eur J Vasc Endovasc Surg* 2005; 30(3): 227-244, incorporated herein by reference. Stabilization of collagen in aneurysm tissue can be an effective aspect for treating vessel damage associated with an aneurysm.

Timely diagnosis of aneurysm can save lives and provides early treatment intervention opportunity. Methods for diagnosing and identifying the degree of aneurysm expansion are available due to developments in high resolution imaging technology such as ultrasound (US), computational tomography (CT), and magnetic resonance imaging (MRI). Various appropriate contrast agents can be used to enhance the imaging. The use of magnetic resonance and CT imaging techniques to guide procedures on aneurysms is described further in U.S. Pat. No. 6,463,317 to Kucharczyk et al., entitled "Device and Method for the Endovascular Treatment of Aneurysms," and U.S. Pat. No. 6,793,664 to Mazzocchi et al., entitled "System and Method of Minimally-Invasive Exovascular Aneurysm Treatment," both of which are incorporated herein by reference.

Additionally, using one or more biomarker(s) to diagnose vascular aneurysm can provide invaluable diagnostic information prior to and after the treatment outlined herein and the diagnostic biomarkers are disclosed in U.S. Patent Application No. 2009/0186370 to Ogle et al. (the '370 application) entitled "Diagnostic Biomarkers for Vascular Aneurysm", incorporated herein by reference. Specifically, recent techniques have been developed to track the progress of the aneurysm using a blood test and/or urine test. Once the aneurysm is identified and has progressed to a stage of initiating treatment, imaging generally is used to identify the location of the aneurysm and to assess the severity of the problem and to identify an approach for the treatment procedure.

Treatment devices and related procedures relating to isolation of a portion of a blood vessel are disclosed in U.S. Pat. No. 8,100,961 (the '961 patent) to Vyavahare et al., entitled "Elastin Stabilization of Connective Tissue", U.S. Patent Application No. 2010/0016833 to Ogle et al. entitled "Devices for the treatment of vascular aneurysm", and U.S. Patent Application No. 2011/0093000 to Ogle et al. entitled "Vascular medical devices with sealing elements and procedures for the treatment of isolated vessel sections, all incorporated herein by references. In contrast with these approaches, coated balloons are described herein that can be used to deliver therapeutic agents to a damaged or diseased portion of a blood vessel based on the balloon coating. In general, connective tissue such as blood vessel targeted with the therapeutic agent(s) or composition(s) can be stabilized so as to be less susceptible to protein degradation as well as to have improved mechanical strength to resist distortion of the natural shape and possible bursting. Evidence suggests that elastin degradation contributes significantly to aneurysm formation and expansion in blood vessels. Elastin stabilization compositions comprising phenolic type compounds have been described in detail in the '961 patent referenced above. The elastin stabilization agents can reduce or eliminate further enzymatic degradation of the tissue and mechanically stabilize the elastin proteins.

Protein crosslinking or stabilization agents are commonly known to bond with certain areas of proteins that are prone to enzymatic attacks. While protein stabilization agents generally are broadly reactive, some agents have some particular specificity for more extensive effective stabilization, which may involve crosslinking, for certain proteins. In particular, structural proteins, such as elastin and collagen, have amino acid sequences that can use high percentages of certain amino acids that are good targets for certain crosslinking or stabilization compositions. Thus, we refer herein to elastin stabilization agents due to preferential bonding to elastin, while the agents may have some bonding with a broad range of proteins. In general, the bonding described herein is not limited to covalent bonding, and the interaction between the stabilization agent and the target protein is not limited to covalent crosslinking. Other interactions between protein and stabilization agent such as hydrophobic interactions, hydrogen bonding, and Van der Waals interaction can be present with or without covalent bonding to stabilize the target protein.

Since elastin comprises a very significant structural component of connective tissue, the stabilization of elastin can be effective at stabilizing blood vessel such as an aneurysm. The stabilization of elastin can be particularly effective using the stabilization compositions described herein that generally protect hydrophobic domains of the elastic protein through steric effects, which are believed to inhibit degradation of the elastin by elastase. Stabilization of elastin can be effectuated using compositions described herein that have little if any general cytotoxicity, so that the compositions can be delivered without excessive risk to the patient through general release of the composition. The devices, compositions and associated procedures described herein are directed to human patients, although these techniques can also be used for farm animals, pets and other mammals. The devices disclosed herein can be directed to localized delivery of therapeutic compositions to the stabilization of the elastin and collagen component of connective tissue, and in particular, blood vessels or other vessels. It should be understood that while a device can be directed in some embodiments to the stabilization of blood vessels susceptible to the formation of aneurysms, in other embodiments, other organs, other diseases and/or other conditions can be treated. In particular, the disclosed coated balloon and treatment protocols may be applicable to any animal or human connective tissue that comprises elastin and/or collagen components.

It is believed that any of a number of natural and synthetic phenolic compounds can bind elastin and thereby protect elastin from degradation, for instance due to the action of elastin degrading enzymes. Accordingly, in one embodiment, devices described herein and corresponding methods can be effectively used to deliver compositions that can inhibit enzyme-catalyzed degradation of elastin, and in particular elastase and/or MMP catalyzed degradation of elastin. Tissue with an elastin component, e.g., blood vessels and other connective tissue, can be stabilized and/or strengthened with a polyphenolic compound, although these compounds can also be used to stabilize a broader range of tissue based on more general protein binding as well as binding to tissues with lower amounts of elastin. In particular, it is believed that any of a number of natural and synthetic phenolic compounds can bind structural proteins and thereby strengthen the corresponding connective tissue, such as blood vessel, and make the tissue less susceptible to enzymatic degradation. Because natural elastin turnover is exceptionally low, it has been hypothesized that PGG may remain bound to vascular elastin for extended periods of time after application with the coated balloon. The bound PGG is believed to be sufficient to maintain resistance to degradation enzymes and to deter aneurysm progression.

In some embodiments, protein crosslinking phenolic compounds include, for example, any compound that comprises at least one phenolic group bound to a hydrophobic core. In general, a phenolic compound described herein comprises a plurality of phenolic groups connected to form a hydrophobic core with peripheral phenolic hydroxyl groups. While not wishing to be bound by theory, it is believed that interaction between the phenolic compound and elastin proteins have aspects involving both the hydroxyl group as well as the hydrophobic core of the molecules. In particular, the large hydrophobic regions of the elastin protein, which are believed to contain sites susceptible to elastase-mediated cleavage, are also believed to be able to interact with the hydrophobic core of the phenolic compound, which would then block the attacks from elastase. Thus, the interaction of the hydrophobic core of the phenolic stabilization compound with the hydrophobic region of the elastin may contribute to inhibition of elastin cleavage by elastase. In certain embodiments, the phenolic compounds can comprise one or more double bonds, with which the phenolic compounds can covalently bind to the structural protein, forming an even stronger protective association between the phenolic compound and the extracellular matrix of the tissue.

Drug coated balloons are known in the art, such as ELUTAX™ (Aachen Resonance), IMPACT FALCON™ (Invatec/Medtronic) and SeQuent® Please (B. Braun). In general, these coated balloons have been dilation balloons that are designed to apply large amounts of pressure to open up a stenosis region in a blood vessel in an angioplasty type procedure to increase flow through a vessel possibly in combination with the delivery of a stent. In contrast, the balloons considered herein are designed to be compliant, such that larger amounts of pressure are not applied to the vessel since the vessel could be damaged due to weakening of the vessel from the disease conditions. Thus, the present balloons have designs selected according to the corresponding parameters for lower pressure operation.

When delivering a drug from a coated stent or other device to be left in a patient, the drug elution can be generally at a relatively slow rate and the coatings can be designed appropriately. In contrast, with delivery from a drug coated balloon, drug delivery generally from a balloon is relatively rapid since the balloon is not kept within the patient for a long period of time. The use of drug microspheres to speed delivery of a drug from a balloon coating is described in published U.S. application 2012/0015019 to Pacetti et al., entitled "Drug Coated Balloon With In-Situ Formed Drug Containing Microspheres," incorporated herein by reference. The use of coating additives to facilitate drug delivery from a coated balloon are described in published U.S. patent application 2008/0255508 to Wang, entitled "Drug Releasing Coatings for Medical Devices," incorporated herein by reference.

To facilitate transfer of the elastin stabilization compositions to a blood vessel wall, the balloon coating can be designed as described herein. Specifically, hydrophilic polymers can be incorporated into the coating to increase the rate of transfer of the elastin stabilization composition from the balloon coating to the vessel wall. The hydrophilic polymer can be placed as a layer under the coating of the elastin stabilization coating and/or in a blend with the elastin stabilization composition with the polymer forming a binder.

While not wishing to be bound by a theory, upon contact with a patient's blood, the presence of a hydrophilic polymer draws fluid into the coating. The interaction of the hydrophilic polymer with the aqueous blood fluid results in the more rapid transfer of the elastin stabilization compositions out from the coating. Due to the contact of the balloon with the blood vessel wall upon deployment, as the elastin stabilization composition leaves the coating, the composition is delivered into the blood vessel wall. Once delivered into the blood vessel wall, the elastic stabilization composition can react with elastin in the extracellular matrix of the blood vessel wall to provide an increase in mechanical strength of the wall and/or to inhibit further degradation of the blood vessel wall. The coating structure can be used to facilitate the transfer of a desired amount of an elastin stabilization composition into a blood vessel wall within a desired time period for a procedure. The ability to transfer in a short period of time a greater amount of elastin stabilization composition can result in more desirable outcome from the procedure.

Before, after or simultaneously with the treatment with elastin stabilization agent, aneurysm may be optionally treated with collagen stabilization agents such as glutaraldehyde to further stabilize the blood vessel. In other words, a collagen stabilization composition can be delivered simultaneously with the elastic stabilization composition in the balloon coating or separately with another coated balloon or with a different type of delivery. Some collagen stabilization compositions, such as glutaraldehyde, are freely soluble in water so that the delivery of these compositions may pose different delivery challenges. Collagen stabilization agent has been reported in U.S. patent application No. 2010/0119605 to Isenburg et al. (the '605 application) entitled "Compositions for Tissue Stabilization", incorporated herein by reference.

Therapeutic compositions can comprise additional agents, in addition to agents that stabilize elastin and/or collagen. Such additional agents can be active agents, providing direct benefit to the tissue, or may be supporting agents, improving imaging, delivery, compatibility, or reactivity of other agents in the composition. For example, the composition can incorporate a gallic acid scavenger, for example ascorbic acid or glutathione, so as to decrease or prevent the release of free gallic acid residues. Also, the therapeutic composition can be combined with any of a number of possible lipid-lowering medications so as to prevent the development of calcified lipid deposits or arteriosclerosis plaques that can often be found in conjunction with aneurysm formation.

The coated balloon can be introduced, for example, using conventional techniques to establish a hemostatic entrance into the artery, generally the femoral artery. In some embodiments, a pretreatment step can be performed before the delivery of the coated balloon. For example, thrombolytic composition can be delivered into the blood vessel to rid of thrombus and to expose vessel tissue for further treatment. To identify the location for placement of the device, appropriate imaging can be performed prior to performing the procedure as well as during the procedure. After the treatment steps have been completed, the operator can deactivate the device by transitioning the coated balloon to a recovery configuration. Once the coated balloon is in a recovery configuration, the operator can withdraw the device from the blood vessel.

Tissue Stabilization Agent

Suitable elastin stabilization agents can include, for example, phenolic compounds with one or more phenol groups extending from the hydrophobic core of the molecule, such as, flavonoids and their derivatives (e.g., anthocyanins, quercetin), flavolignans, phenolic rhizomes, flavan-3-ols including (+)-catechin and (−)-epicatechin, other tannins and derivatives thereof (such as tannic acid, pentagalloylglucose, nobotanin, epigallocatechin gallate, and gallotannins), ellagic acid, procyanidins, and the like. Suitable phenolic compounds include synthetic and natural phenolic compounds. For example, natural phenolic compounds can include those found in extracts from natural plant-based sources such as extracts of olive oil (e.g., hydroxytyrosol (3,4-dihydroxyphenylethanol) and oleuropein, extracts of cocoa bean that can contain epicatechin and analogous compounds, extracts of *Camellia* including *C. senensis* (green tea) and *C. assaimic*, extracts of licorice, sea whip, aloe vera, chamomile, and the like.

In some embodiments, the phenolic compounds can be tannins and derivatives thereof. Tannins can be found in many plant species. For example, the tea plant (*Camellia sinensis*) has a naturally high tannin content. Green tea leaves are a major plant source of tannins, as they not only contain the tannic and gallic acid groups, but also prodelphinidin, a proanthocyanidin. Tannins are also found in wine, particularly red wine as well as in grape skins and seeds. Pomegranates also contain a diverse array of tannins, particularly hydrolysable tannins.

Pentagalloylglucose (PGG) and tannic acid (TA) are members of the tannin family, a group of naturally derived polyphenolic compounds. PGG is a less toxic derivative of tannic acid. PGG is naturally occurring, relatively non-toxic and not expected to exhibit significant side effects. PGG is characterized by a D-glucose molecule esterified at all five hydroxyl moieties by gallic acid (3, 4, 5-trihydroxybenzoic acid) as shown in FIG. 1. In general, it is understood that the PGG molecule can also have 1-4 galloyl group(s) and the galloyl groups can assume different stereo chemical forms. For example, PGG can be in either alpha or beta forms. It has been reported that periarterial treatment with PGG preserves elastin fiber integrity and hinders aneurysmal dilatation of the abdominal aorta in a clinically relevant model of aortic aneurysms. See the detailed discussion of formulations and compositions for connective tissue stabilization through the use of elastin stabilization agents disclosed in the '961 patent cited above, incorporated herein by reference.

In further embodiments, the elastic stabilization composition can be combined with another composition to stabilize the coating for delivery. For example, the elastin stabilization composition can be combined, for example with a hydrogel, and the association of the composition with a hydrophilic hydrogel can facilitate delivery of the relatively hydrophobic composition into the adjacent tissue after expansion of the coated balloon. The use of hydrogels as a delivery vehicle in other contexts for the delivery of elastin stabilization compositions is described further in published U.S. patent application 2009/0214654 to Isenburg et al., entitled "Treatment of Aneurysm with Application of Connective Tissue Stabilization Agent in Combination with a Delivery Vehicle," incorporated herein by reference.

For stabilization compositions that are expected to impart a fast and strong binding thus stabilization effect, relatively high concentration of elastin stabilization agents maybe used. Toxicity reduction in these relatively high concentration cases can be especially of interest. For example, when tannin family of compounds such as PGG or TA is used, it can be desirable to maintain low level of free or unbound gallic acid in the composition. In some embodiments, the composition can comprise little or no unbound gallic acid. In some embodiments, the composition can comprise no more than about 5 wt % unbound gallic acid. In further embodiments, the composition can comprise no more than about 2.5 wt % unbound gallic acid and in additional embodiments no more than about 1 wt % unbound gallic acid. A person of ordinary skill in the art will recognize that additional ranges of concentration within the explicit ranges above are contemplated and are within the present disclosure.

In addition to the elastin stabilization agents, the coatings can further comprise other therapeutic agents or the like. For example, the coatings can comprise, for example, antibiotics, anti-inflammatories, thrombolytic agents, ACE inhibitors, calcium agonists, lipid modifying agents, combinations thereof or the like. Lipid modifying agents can include, for example, statins such as atorvastatin, fluvastatin, lovastatin, pitavastatin, pravastatin, rosuvastatin, and simvastatin; niacin; fibrates such as bezafibrate, ciprofibrate, clofibrate, gemfibrozil, and fenofibrate; or combinations thereof. Thrombolytic agents can include, for example, heparin, aspirin, adenosine diphosphate receptor antagonists, Gp IIb/IIIa inhibitors or combinations thereof. Angiotensin converting enzyme (ACE) inhibitors may inhibit oxygen-free radical production and promote normal endothelial function. ACE inhibitors include, for example, captopril, zofenopril, enalapril, ramipril, quinipril, fosinopril and combinations thereof.

Suitable antibiotics are disclosed for example in U.S. Pat. No. 6,847,848 to Sterzer et al. entitled: "Inflatable Balloon Catheter Structural Designs and Methods for Treating Diseased Tissue of a Patient", U.S. Pat. No. 5,269,770 to Conway et al. entitled: "Microcidal Agent Releasing Catheter with Balloon", and U.S. Pat. No. 6,293,923 to Yachia et al. entitled: "Intravesicular Balloon", all incorporated herein by reference. Suitable anti-inflammatory agents are disclosed, for example, in U.S. Pat. No. 7,658,966 to Kokish et al. entitled: "Balloon Catheter for Delivering Therapeutic Agents", U.S. Pat. No. 7,314,480 to Eidenschink et al. entitled: "Rotating Balloon Expandable Sheath Bifurcation Delivery", U.S. Pat. No. 7,060,051 to Plasis et al. entitled: "Multi-balloon Catheter with Hydrogel Coating", and U.S. Pat. No. 5,102,402 to Dror et al entitled: "Releasable Coatings on Balloon Catheters", all incorporated herein by reference.

With respect to providing mechanical stabilization of blood vessel, collagen crosslinking/stabilization compositions have been found to provide a high degree of stabilization of connective tissues, as described in the '605 application cited above. Multi-functional reagents, such as glutaraldehyde, diamines, genipin, acyl azide, and epoxyamines, are known to cross-link functional groups in collagen thereby to stabilize tissue having a collagen component. Some known functional groups for collagen crosslinking are amino, thiol, hydroxyl, and carbonyl in collagen and/or other proteins, such as other structural proteins. By binding to and crosslinking collagen and/or other proteins, the multi-functional agents can increase the mechanical strength of the blood vessel. Blood vessel treated with collagen crosslinking/stabilization agent with or without combination with elastin stabilization agent may exhibit enhanced rupture resistance, resistance to enzymatic degradation such as elastase and collagenase, and a higher thermal denaturation temperature. In some embodiments, a collagen crosslinking/stabilization agent such as glutaraldehyde can be used as a single stabilization agent to treat the blood vessel before or after the treatment with the elastin stabilization agent such as PGG. In additional or alternative embodiments, a collagen crosslinking agent such as glutaraldehyde can be effectively combined with an elastin stabilization agent such as PGG in the therapeutic composition of the coating layer of the coated balloon.

The therapeutic composition disclosed herein can comprise one or more buffers. For example, a composition having a pH from about 4.0 to about 9.0 may be formulated with inclusion of purified water, saline and a biocompatible buffer, such as phosphate buffers, borate buffers, HEPES, PIPES, MOPSO or combinations thereof. In one embodiment, a composition of the invention may be formulated to have a pH of between about 5.5 and about 7.4. Therapeutic compositions can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, the composition can contain minor amounts of auxiliary substances such as wetting or emulsifying agents, pH buffering agents and the like that can enhance the effectiveness of the vessel stabilizing compound. Coating materials such as lecithin can also be used. These compositions may also contain adjuvants such as preservatives, wetting agents, emulsifying agents and dispersing agents. The therapeutic compositions should be appropriately sterile at the time of use.

Coated Balloon Device

The balloon architecture generally accounts for effective delivery of a therapeutic agent to a diseased or damaged blood vessel with modest risk to the vessel. The therapeutic agent can be delivered from a coating that is designed to deliver the therapeutic agent in a relatively rapid but controlled way so that the therapeutic agent is delivered with a relatively high yield to the vessel wall within a reasonable period of time. To reduce costs, procedure time and risk to the patient, it is desirable to have the therapeutic compositions delivered relatively rapidly to the vessel wall. Also, for delivery to a diseased and/or damaged wall, the balloon can be compliant so that excessive pressure is not applied to the vessel wall. Excessive pressure can rupture a diseased or damaged vessel, such as at an aneurysm, so that the compliant balloons are in significant contrast with coated angioplasty balloons that are specifically designed to open constrictions in blood vessel through the application of significant amounts of pressure. The balloon can be associated with an appropriate catheter to control atraumatic delivery and deployment of the balloon.

A balloon device can comprise a catheter with fittings at the proximal end and the coated balloon attached at or near the distal end. The device can optionally comprise one or more additional components, such as a by-pass lumen, a guide lumen, radiopaque markers, a distal wire and/or other features to facilitate delivery or use of the device. The proximal fittings can generally provide for delivery and subsequent removal of a fluid to the balloon to accomplish the expansion and deflation of the balloon at selected times, and the fittings can also provide hemostatic access to any other lumen within the catheter. An appropriate reservoir, such as a syringe can be connected to the fittings to provide the fluid for inflation of the balloon. The balloon can be designed to have an appropriate size, shape and material to function as a compliant balloon and to deliver the therapeutic composition in the coating to the appropriate location in the vessel. The balloon generally has an inflatable polymer structure in a sealed relationship with the catheter, and a desirable cylindrical shape for the inflatable polymer structure is described further below.

A coating can be applied over the all or a portion of an outer surface of the inflatable polymer structure. For example, for the roughly cylindrical shaped balloon structure, the coating may be applied on the cylindrical walls with the ends of the structure having no coating or only a coating over a portion of the ends since the ends generally do not contact the vessel wall. The coating can comprise a single layer or a plurality of layers to facilitate the relatively rapid delivery of the therapeutic composition, as described further below. In particular, in some embodiments, the balloon is compliant so that balloon does not apply excessive force against the vessel walls and so that the balloon can conform to blood vessel walls that are irregular, which can result from the aneurysm condition or other maladies. With respect to medical balloons, compliance refers to the balloon's diameter change as a function of pressure within the balloon. Low pressure compliant balloons expand significantly upon inflation with a modest amount of pressure. For compliant balloons, suitable elastic polymers, such as thermoplastic elastomers, can be used to form the balloon include, for example, Pebax® (poly(ether-block-amide)), low durometer polyurethanes, styrene-butadiene copolymers, latex, polyisoprene, synthetic rubbers and the like. Compliant balloons generally are not used to expand vessels, and the balloons can be designed to conform to the vessel without applying excessive pressure to the vessel walls.

As noted above, balloons with a generally cylindrical expanded shape can be desirable for delivery of therapeutic compositions in a coating while not applying excessive pressure to the vessel walls. In embodiments with an approximately cylindrical shape, the distal end and the proximal end of the coated balloon can be concave or cupped to provide desirable mechanical performance to the compliant balloon. Specifically, the coated balloon can have concave shaped distal and proximal ends, which are connected by an approximately cylindrical surface in the expanded configuration. The approximately cylindrical surface can conform relatively naturally to the vessel wall. The concave ends of the balloon assist with the balloon conforming to a particular vessel wall without applying excessive pressure on the wall, such as near the edges of the cylinder. In particular, the balloon can conform through distorting at the concave ends to reduce localized pressures on the wall. The coated balloon can similarly be formed from a compliant polymer material that assists with the distribution of forces along the vessel wall. Using the improved balloon design, the risk of damaging fragile vessel walls can be diminished.

The coated balloons can be delivered on a balloon catheter that has an inflation lumen for the delivery of an inflation medium from near the proximal end of the catheter to inflate the compliant balloon. For example, a buffered saline or other suitable inflation liquid can be used. The delivery of an elastin stabilization agent using a leaky balloon has been described previously in the '961 patent, cited above. The coated balloon described herein can provide for a more controlled delivery of the elastin stabilization agents with direct delivery into the tissue. The coated balloon can be designed with a perfusion lumen or by-pass channel to provide for blood flow past the expanded balloon so that the balloon can be left safely in an expanded configuration for a relatively longer period of time. In some embodiments, the coated balloon additionally may be constructed to "weep" liquid from the balloon through the coating so the therapeutic composition in the coating can be delivered from the coating to the surrounding blood vessel more effectively.

For AAA applications, the catheter used for the balloon delivery has a diameter from about 3 French to about 14 French, in some embodiment the diameter is from about 4 French to about 12 French, in further embodiments from about 5 French to about 10 French, and in additional embodiments from about 6 French to about 8 French. The balloons used can have a cylindrical shape with the length of the cylindrical shape ranges from about 20 mm to about 160 mm, in some embodiments from about 30 mm to about 120 mm, in further embodiments from about 40 mm to about 80 mm, and in additional embodiments from about 50 mm to about 70 mm. The inflated but un-expanded balloon in general has a diameter of about 20 mm, in some embodiments from about 10 mm to about 80 mm, in further embodiment from about 15 mm to about 60 mm, and in additional embodiments from about 25 mm to about 35 mm. A person of ordinary skill in the art will recognize that additional size ranges within the explicit ranges above are contemplated and are within the present disclosure. Note that the balloon may be folded, wrapped or otherwise positioned for delivery to the location for deployment in a delivery configuration, which is significantly smaller compared to the inflated but unexpended sizes discussed above. Additionally, in the expanded configuration, the diameter of the balloon can be increased by about 25% to about 2000%, in some embodiment, by about 50% to about 1500%, in additional embodiment, by about 75% to about 1250%, in further embodiment, by about 100% to about 1000%. A person of ordinary skill in the art will recognize that additional increase by percentage ranges within the explicit ranges above are contemplated and are within the present disclosure.

Throughout the specification, the balloons are discussed under the context of different configurations. It is understood that the delivery or un-extended or un-inflated configuration in general refers to balloons in a compress or folded configuration that is generally used during the delivery process. The inflated but unexpanded configuration refers to the nominal configuration of the balloon that is used during the coating and other surface modification processes described herein. The inflated but unexpanded configuration is also used in the figure illustrations to present the construction of the balloon. The expanded configuration in general refers to the deployed state of the balloon during the therapeutic process. It is also used in the figure illustrations to present the details of the coating and other features of the balloon. Additionally, the recovery or low profile configuration in general is used to describe the balloon during the retrieval process that is not inflated and not necessarily as compressed as the delivery configuration.

Figure 2:
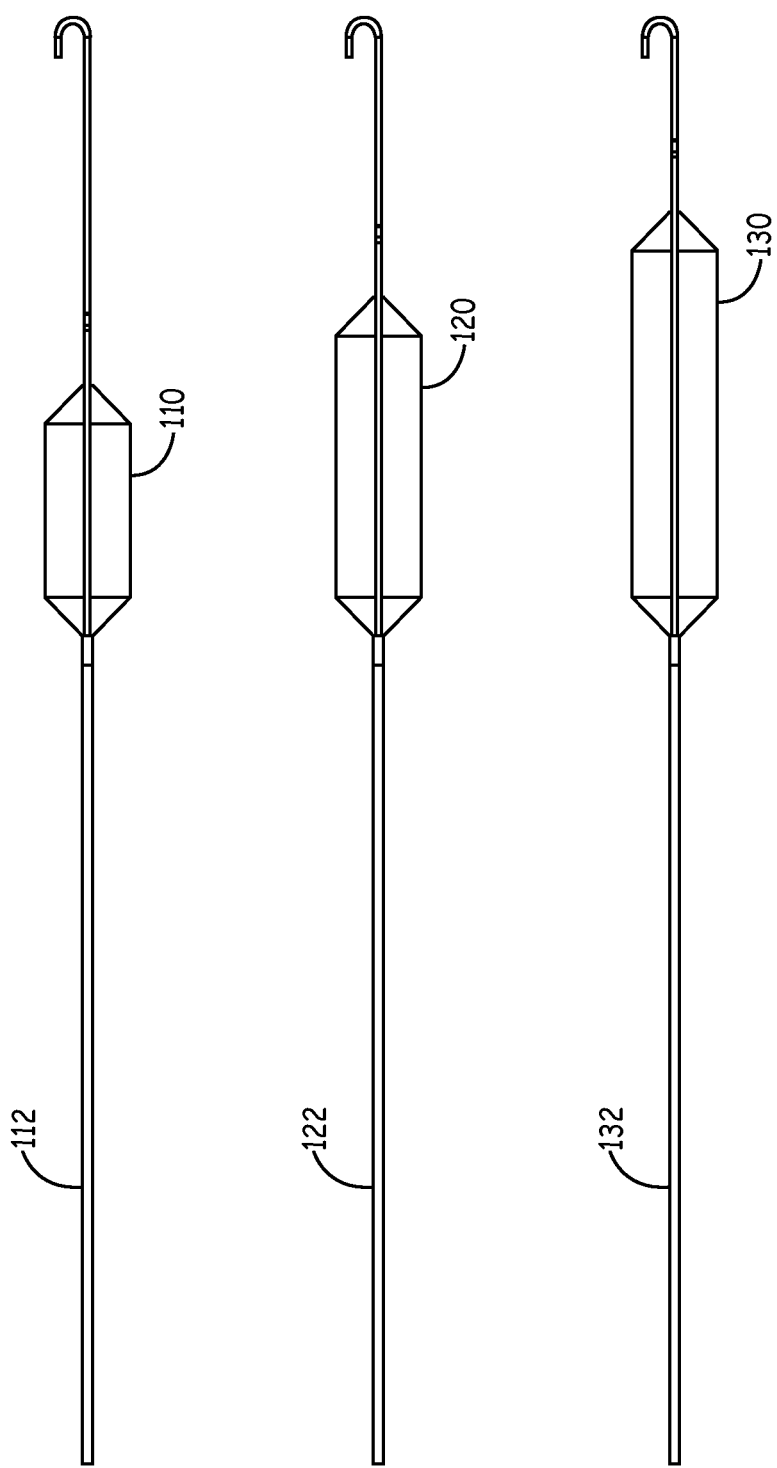
FIG. 2 is a fragmentary side view of coated balloon devices with balloons in three different lengths in an inflated but unexpanded configuration. Balloon catheters are truncated so that the distal end of the device is not depicted.

Referring to FIG. 2, coated balloons 110, 120, and 130 are shown with three different lengths 40 mm, 60 mm, and 80 mm respectively. The balloons are shown in an inflated but un-expanded configuration having a diameter of 20 mm, which is expandable to 60 mm in a deployed configuration. For commercial coated balloons, sets of sizes can be available for a physician to select a desired size for a particular patient, such as the three balloons shown in FIG. 2. In further embodiments, sets of two balloons, four balloons, five balloons or more than five balloons can be distributed, and different balloon sizes can have a different length and/or a different expanded diameter from other members of the set. The coated balloons 110, 120, and 130 are attached to delivery catheters 112, 122, and 132, respectively. The delivery catheters can have a diameter from about 5 French to about 12 French, in some embodiments from about 6 French to about 11 French, and in additional embodiments from about 7 French to about 10 French, although other catheter diameters can be used as desired.

Depending on the length of delivery time of the stabilization composition from the coating and the location of the section of the blood vessel to be treated, a perfusion lumen or by-pass channel may or may not be desirable in the coated balloon device. In some embodiments, the by-pass channel may be present in the catheter shaft. In some embodiments, a by-pass channel 154 may be present in a balloon body 150 as shown in FIGS. 3A and 3B, with FIG. 3B showing the enlarged balloon of FIG. 3A. As shown in FIGS. 3A and 3B, the treatment balloon may optionally have circumferential zone of pores 156 for weeping an expansion fluid delivered to expand the balloon, which can be for example saline, although a stabilization agent can be also delivered if desired. In this embodiment, a guidewire 151 extends through guidewire lumen 153, as shown in the enlarged view in FIG. 3B. The balloon 150 is attached to a catheter 152 that comprises a balloon lumen 155 for the delivery of saline or other inflation fluid through port 157 to provide fluid communication with the interior of balloon 150. Balloon 150 has concave ends 159, 161.

As noted above, the concaved or cupped ends can allow the coated balloon to be flexible while maintaining tight seal against a vessel wall to provide for desired transfer of a therapeutic composition into the vessel wall. The flexible coated balloon design is aimed to reduce or eliminate any trauma the coated balloon may have on the vessel that it is already weakened by aneurysm or other condition. The proximal and distal concaved ends of the coated balloon may be of same size and shape or of different size and shape as each other. In general, the volume of the concaved end, which can be evaluated using a planar surface to close the end, each may have a volume of about 5% to about 35%, in some embodiments about 8% to about 25%, and in further embodiments from about 10% to about 20% relative to the balloon with planar ends rather than the concave ends. The dimension of the concaved ends outlined above may change once the balloon is deployed inside the vessel and subject to outside pressure. The concave ends can have any reasonable desired shape, such as hemispheres, conical shapes or a non-specific geometrical shape. A person of ordinary skill in the art will recognize that additional ranges of dimensions within the explicit ranges above are contemplated and are within the present disclosure. The special shape of coated balloon in FIGS. 3A and 3B is designed to provide tight and flexible contact against the vessel walls when inflated. This is particularly beneficial when treating aneurysm in major arteries where pulsation of the artery wall may make maintaining contact between the deployed coated balloon and the vessel walls difficult while the vessel walls may be also fragile due to degradation of the vessel tissue. Compliant medical balloon with a generally cylindrical shape and concave ends for use as sealing members are described in published U.S. patent application 2011/0093000 to Ogle et al., entitled "Vascular Medical Devices With Sealing Elements and Procedures for the Treatment of Isolated Vessel Sections," incorporated herein by reference.

The balloon device, such as the catheter and fittings, can be formed from one or more biocompatible materials, including, for example, metals, such as stainless steel or alloys, e.g., Nitinol®, or polymers such as polyether-amide block co-polymer (PEBAX®), nylon (polyamides), polyolefins, polytetrafluoroethylene, polyesters, polyurethanes, polycarbonates or other suitable biocompatible polymers. Radio-opacity can be achieved with the addition of markers, such as platinum-iridium or platinum-tungsten or through radio-pacifiers, such as barium sulfate, bismuth trioxide, bismuth subcarbonate, powdered tungsten, powdered tantalum or the like, added to the polymer resin. Generally, different sections of the device can be formed from different materials from other sections, and sections of the device can comprise a plurality of materials at different locations and/or at a particular location. Suitable materials for the compliant balloon structure are described above.

The coating can be designed for effective controlled delivery to the targeted tissue along the interior of a blood vessel, such as the aorta. The amount of elastin stabilization agent can be selected to be effective at stabilizing the tissue, and the coating material can be selected to give controlled delivery of the stabilization agent. In particular, it is desirable for the coating material to be delivered relatively quickly once the balloon is expanded and the tissue is contacted with the coating, but it is similarly desired for the coating material to stay on during the delivery and not be released prior to expansion of the balloon. The balloon structure and/or additional layers of a coating material can facilitate the controlled delivery of the agent. Since the coating is applied to a compliant balloon, the coating generally can be somewhat elastic also so that the coating expands to some degree with the balloon, although the coating may not necessarily be as elastic as the balloon for appropriate delivery of the stabilization agent.

When the balloon is delivered, it is desirable for the stabilization agent associated with the coating to be delivered to the tissue relatively quickly to limit the procedure time. On the other hand, it is desired that the therapeutic composition is not delivered prematurely while the balloon is being guided through the vessel to the location of the vessel selected for delivery of the stabilization agent. To reduce or eliminate premature release of the stabilization agent while not extending the delivery time beyond desired amounts, the coating with the elastin stabilization agent can be protected with a sacrificial top-coating or with a mechanical cover. A sacrificial top-coating can comprise a hydrophilic composition that dissolves in a controlled way, such as within 30 seconds to a couple of minutes upon exposure to blood flow within a vessel. Suitable hydrophilic top-coat compositions can comprise, for example, sugars, sugar derivatives and the like, which can be delivered safely into a patient. In some embodiments, the coated balloon device may additionally comprise a sheath to cover the coated balloon in the delivery or unextended or un-inflated configuration. Upon delivery of the sheath covered coated balloon device at the desired location in the blood vessel, the sheath is made to slide off the coated balloon to expose the balloon device for subsequent deployment and treatment procedures. In further embodiments, the balloon can comprise a mechanical cover structure that opens upon expansion of the device. For example, an elastic cover material can have stripes, pores or fenestrations that are effectively closed in the delivery or un-extended configuration that open upon stretching when the balloon is expanded. An example of a fenestrated cover over the coating is presented in FIG. 4 as discussed in the following. In general, when applying top coat to the coated balloon, some degree of dissolution of the coating of the balloon can occur. Although dissolution of the coating of the balloon when applying top coat is to be reduced or avoided, some degree of dissolution may be acceptable. Specific solvents can be selected to keep dissolution to acceptable levels. In some embodiments, electrostatic coating or plasma coating methods may be used to apply top coat to avoid or lessen the impact to the coating layer that is already in place and dry. In other embodiment, spray coating or very quick dip coating techniques may be used to deposit the top coat on the surface of the coated balloon.

A mechanical cover over the coating of the stabilization agent can be provided with a dual layer balloon 160 as shown in FIG. 4A in which the coating 164 is placed between the balloon layers with a balloon outer layer 170 that comprises an elastic material that is fenestrated. Upon expansion of the balloon 160 as shown in FIG. 4B, the openings or slits 166 through the outer balloon layer opens to substantially expose the coating 164 to the tissue surrounding the balloon so that the stabilization composition can be transferred to the tissue of the blood vessel. The fenestrated outer balloon can be constructed with slits 166 cut through the outer balloon layer. The sated outer balloon 170 can be assembled to completely or essentially completely cover the coating in the inflated but unexpanded configuration on the catheter. Upon expansion, the slits 166 open to expose the coating 164. A cross sectional view of the balloon 160 taken along the line C-C of FIG. 4B is shown in FIG. 4C, showing the coating 164 sandwiched between the outer balloon 170 and the inner balloon 168, with the slits 166 open to expose the coating 164. The balloon is shown to be associated with a guidewire 162 in FIGS. 4A-4C. In additional or alternative embodiments, the fenestrated outer balloon of the covered balloon design can comprise holes or pores through the outer balloon that are small in the inflated but un-expanded configuration so that the coating is substantially protected during delivery, and the pores can naturally expand with the outer balloon due to the elastic nature of the material to expose the coating through the expanded pores upon expansion of the outer balloon.

Also, an unexpanded balloon 180 can comprise ridges 186 that are filled with coating material on the surface 190 of the balloon as shown in FIG. 5A. In some embodiments, the ridges 186 can remain effectively closed until the balloon is expanded to expose the coating 184 within the ridges as shown in FIG. 5B. A cross sectional view of the balloon 180 taken along the line C-C of FIG. 5A is shown in FIG. 5C, showing the coating 184 enclosed in the ridge 186 of the balloon surface 190. The balloon is shown to be associated with a guidewire 182 in FIGS. 5A-5C.

Figure 6A:
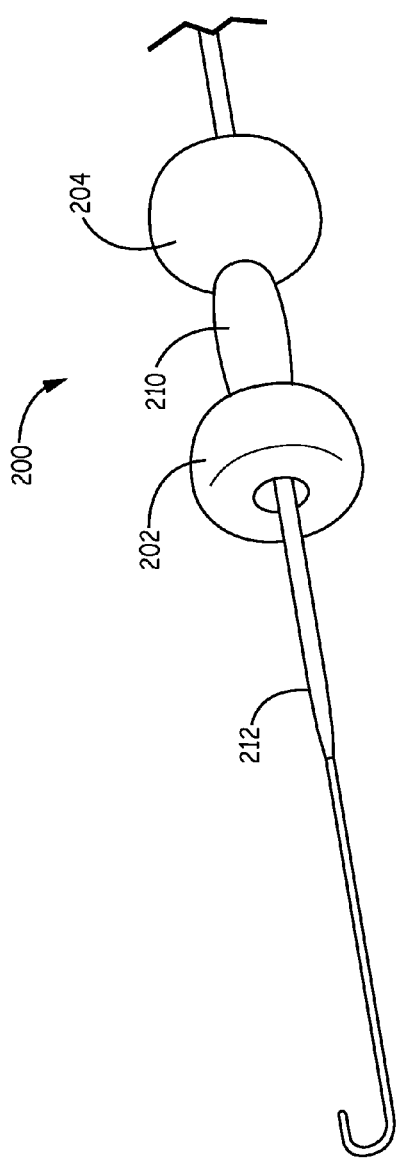
FIG. 6A is a fragmentary perspective view of a balloon complex with a deployed proximal balloon, a deployed distal balloon, and a sponge material covered middle balloon that is not deployed.
Figure 6B:
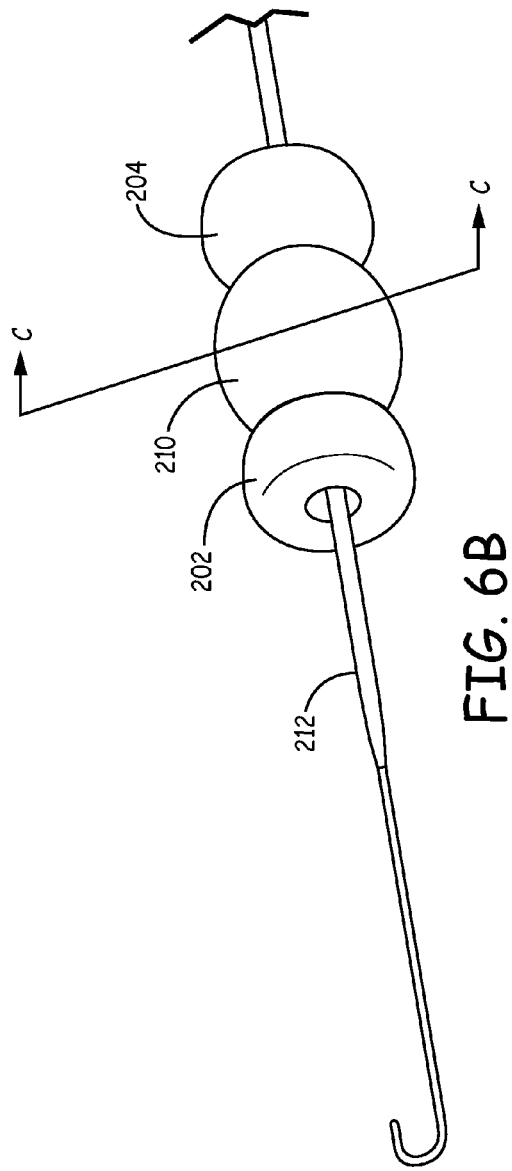
FIG. 6B is a fragmentary perspective view of the balloon complex of FIG. 6A with the extended middle balloon covered with extended sponge material.
Figure 6C:
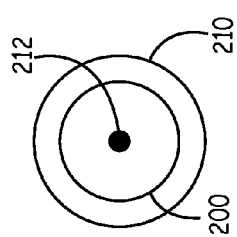
FIG. 6C is a cross sectional view of the balloon along the C-C line of FIG. 6B.

Furthermore, the coating with the stabilization composition can comprise a sponge material that further controls release of the stabilization composition and/or a retrievable stent like structure along the exterior of the balloon. Expandable medical devices with a sponge coating are described in published U.S. patent application 2009/0069883 to Ding et al., entitled "Medical Device With Sponge Coating for Controlled Drug Release," incorporated herein by reference. The coated balloons described herein can be incorporated into devices with other structures to facilitate the delivery process. For example as shown in FIGS. 6A and 6B, a center balloon 200 with a sponge element 210 can be interfaced with a distal balloon 202 and a proximal balloon 204. The distal balloon 202 and the proximal balloon 204 together when deployed or inflated as shown in FIG. 6A, effectively isolate an area of interest in the vessel for exposure to the coated center balloon 200. The center balloon 200 can then be inflated or deployed as shown in FIG. 6B to deliver stabilization composition to the isolated treatment area. A cross sectional view of the balloon 200 taken along the C-C line of FIG. 6B is shown in FIG. 6C, showing the sponge coating 210 outside the center balloon 200 in an expanded configuration The balloons are shown to be associated with a guidewire 212 in FIGS. 6A-6C.

The balloon architecture can be designed to facilitate delivery of the stabilization composition from the coating. As noted above, it is desirable to deliver the stabilization agent in a reasonably short period of time to correspondingly limit the time of the procedure. The coating composition itself can be designed to transfer the stabilization composition relatively quickly, and such a design can be supported through the protection of the coating prior to expansion of the balloon as described above. In addition, a hydrophilic undercoating can be placed below the coating with the stabilization composition. Stabilization agents of particular interest tend to be relatively hydrophobic, so the placement of a hydrophilic undercoating below the relatively hydrophobic stabilization composition tends to drive the relatively hydrophobic stabilization composition off from the balloon upon exposure to blood in the vessel. In additional or alternative embodiments, the balloon can have small pores for a slow weep of expansion fluid used to expand the balloon such as pores 156 shown in FIGS. 3A and 3B. A relatively small amount of saline or other fluid through the balloon can also facilitate the transfer of the stabilization composition from the balloon to the adjacent tissue.

While the use of a coated balloon inherently limits the delivery of stabilization composition away from the blood vessel tissue contacting the balloon, it can be desirable to capture some of the stabilization composition that does migrate away from the site through the vessel. Flow through the vessel generally is occluded at least partially if the balloon includes a perfusions lumen or essentially completely if the balloon does not include a perfusion lumen. A perfusion lumen can also be referred to as a by-pass channel. In either case an appropriate structure can be placed in the vessel to capture the composition. For example, either another balloon or a filter can be deployed distal to the coated balloon, and the capture device can comprise a capture coating that binds to the stabilization composition either through a specific binding interaction, through a hydrophobic interaction, or any other known molecular interactions.

Coating Formation

In general, the phenolic compounds described herein can be provided in a biocompatible coating composition that stabilizes the vessel wall following delivery into the vessel wall. For instance, compositions disclosed herein can comprise one or more phenolic compounds in a concentration that can vary over a wide range, and in some embodiments, a PGG polymer can be used in the coating in essentially pure form. In particular, PGG can form a polymer that can be incorporated into the coating for delivery into the vessel wall. The phenolic compound such as PGG can be additionally mixed with a hydrophilic polymer such as polyvinyl alcohol (PVA) to form a therapeutic stabilization coating composition, which can be applied directed to the surface of a balloon to form a coating layer. For example, in some embodiments, the therapeutic composition incorporated into the coating can comprise one or more phenolic compounds that are from about 5 wt % to about 100 wt % of the total therapeutic composition, in further embodiments from about 20 wt % to about 90 wt %, and in additional embodiments from about 30 wt % to about 80 wt %. PGG is a particularly desirable composition for delivery, and it can be desirable to use PGG alone as the therapeutic composition loaded into the coating. As noted above, polymerized PGG can be used alone as the coating without a polymer matrix to further support the coating. However, when a polymer matrix is used for the coating, the ratio between the therapeutic composition and the hydrophilic polymer can in some embodiments range from about 1:19 to about 20:0, in further embodiments from about 1:4 to about 10:1, in additional embodiments from about 3:7 about 7:3. A person of ordinary skill in the art will recognize that additional concentration or ratio ranges within the explicit ranges above are contemplated and are within the present disclosure.

The coating composition can be directly applied on the balloon surface to form the coating layer. In some embodiments, the coating formation of the coated balloon described herein can start with treating the balloon surface to improve its affinity to the coating composition. For example, the balloon surface can be cleaned with a solvent like methyl or ethyl alcohol, isopropyl alcohol, a ketone solvent like methyl ethyl ketone or hexane. Other surface treatments such as plasma treating can also be used. The balloon with the cleaned surface can be simply referred to as modified balloon or pre-treated balloon. In some embodiments, it maybe desirable to have an undercoat layer on the surface of the balloon before the application of the coating composition to form the coating layer. For example, an aliphatic diisocyanate such as diisocyanatohexane or its higher analogs with or without heteroatoms in the hydrocarbon chains can be used to help anchor a hydrophilic polymer such as polyvinyl alcohol (PVA) and/or polyethylene glycol (PEG) through a hydroxy group of the polymer on the surface of the balloon to form an undercoat layer before the balloon can be coated with the therapeutic composition that comprises a stabilization compound such as PGG. Such aliphatic diisocyanates can also be used to anchor other hydrophilic polymers that carry primary or secondary amine groups to the surface of the balloon if needed. In general, a hydrophilic polymer solution comprises water and alcohol in a blend as the solvent. Suitable alcohols include low molecular weight aliphatic alcohols, such as isopropyl alcohol, ethanol, butanol and the like. In some embodiments, the balloon surface is treated with an aliphatic diisocyanate such as hexamethylene diisocyanate then reacts with a solution of PVA in water and isopropyl alcohol.

PVA is known to hydrate in seconds or minutes upon contact with blood. For balloon without undercoat, the coated balloon comprises a coating layer that comprises PGG and PVA directly on the balloon surface. For modified balloon with undercoat, the coated balloon thus comprises a coating layer that comprises PGG and PVA and an undercoat layer comprising PVA. Upon hydration, the polymer in the undercoat layer may adhere to the PVA in the coating layer to prevent the delamination of the coating from the balloon while the therapeutic compositions, which generally comprises PGG, is released into the wall of the blood vessel such as aorta as the balloon is expanded to make contact with the aneurismal segment. Because of the relative hydrophobic nature of PGG, hydration of the relatively hydrophilic PVA in the coating as well as the undercoat may propel the PGG to leave the coating layer and be associated with the tissues of the blood vessel in contact with the coated balloon surface as the tissue of blood vessel is known to be more hydrophobic than blood in general. Because generally compliant balloon is used, the stretching of the compliant balloon can further promote hydration of PVA and releasing of PGG as well.

Although coated balloons with hydrophilic undercoat is used as an example, coated balloons without undercoat layer can also be constructed. The coated balloon without an undercoat layer comprises a coating layer directly attached to the surface of a balloon. Therapeutic composition such as elastin stabilization agent is delivered into the blood vessel through the contact of the coating layer of the coated balloon and the wall of the blood vessel. Alternate polymers in place of PVA to be used in the coating layer as well as the undercoat layer include poly ethylene glycol (PEG), polyvinyl pyrrolidone, poly(lactic-co-glycolic acid) (PLGA), or a combination thereof. In general, the hydrophilic polymer used should be miscible with PGG to form a coating solution to be applied on a balloon surface with or without the undercoat. The hydrophilic polymer in general hydrates quickly and is not prone to delamination to cause potential embolization. In the case of coated balloons with an undercoat, the coating layer and the undercoat layer may or may not use the same hydrophilic polymer.

Balloons used for coating purposes in general can be purchased from commercial sources such as Vention/Advanced Polymer. The coating comprising the therapeutic composition can have an average thickness on the balloon prior to expansion of the balloon from about 5 microns to about 200 microns, in further embodiments from about 10 microns to about 100 microns and in additional embodiments from about 20 microns to about 50 microns. A person of ordinary skill in the art will recognize that additional thickness size ranges within the explicit ranges above are contemplated and are within the present disclosure. Reference to the balloon prior to expansion involves a balloon inflated to its unexpanded size although prior to expansion, the balloon may be folded, wrapped or otherwise manipulated to a low profile for delivery. Similarly, an undercoat or a topcoat can independently have an average thickness on an unexpanded balloon from about 1 micron to about 100 microns, in further embodiments from about 2 microns to about 75 microns and in additional embodiment from about 5 microns to about 50 microns. The ratio of average thicknesses of the therapeutic coating to the undercoat can range from about 1:1 to about 10:1, in further embodiments from about 2:1 to about 8:1 and in additional embodiments from about 3:1 to about 7:1. The ratio of average thicknesses of the therapeutic coating to the top coat can range from about 1:1 to about 10:1, in further embodiments from about 2:1 to about 8:1 and in additional embodiments from about 3:1 to about 7:1. Additionally, the thickness ratio of the undercoat layer, the coating layer, and the top coating can range from about 30:40:30 to about 10:85:5. A person of ordinary skill in the art will recognize that additional ranges within the explicit ranges are contemplated and are within the present disclosure.

With respect to performing the coating process, the appropriate coating solutions can be formed in solvents compatible with the balloon material. The coating solutions can then be applied to the balloon in sufficient quantities to form the desired coating upon drying. The amount of solutions to achieve a desired coating depends on the concentration of the solution. In general, a coating solution comprising a hydrophilic polymer and PGG can comprise water and alcohol in a blend as the solvent. Suitable alcohols include low molecular weight aliphatic alcohols, such as isopropyl alcohol, ethanol, butanol and the like. An undercoating composition can be applied using a suitable solvent for the appropriate polymers, such as methyl ethyl ketone, acetone or the like. The coating can be performed, for example, using dip coating, spray coatings or the like. Dip coating for the application of a polyisocyanate undercoat and a hydrogel overcoat to a balloon is described in U.S. Pat. No. 5,304,121 to Sahatjian, entitled "Drug Delivery System Making Use of a Hydrogel Polymer Coating, incorporated herein by reference. The submersion and the withdrawal processes of the dip coating can be repeated multiple times to build up a desired amount of coating material on the surface of the balloon.

In some embodiments, the surface of a balloon can be treated with an aliphatic diisocyanate such as hexamethylene diisocyanate in a volatile solvent so one of the isocyanate groups bind to the urethane linkages on the balloon surface, leaving the other isocyanate group available for further reaction. The diisocyanate treated balloon can then react with a solution of polyvinyl alcohol (PVA) to bind the PVA to the available isocyanate group on the surface of the balloon. Examplatory solvent for PVA include methyl ethyl ketone (MEK) that has been reported by Sahatjian et al. in U.S. Pat. No. 5,304,121 as a solvent to make the solution of PVA. A water and isopropyl alcohol blend can also serve as a suitable solvent. The balloon surface is thus modified with PVA via a diisocyanate linkage. The PVA modified balloon can then dry in an oven for example at 85° C. for 30 min.

The treatment of the balloon surface before the actual coating formation described above is optional. In some embodiments, a balloon may be coated directly with a solution comprising a therapeutic phenolic compound, e.g. PGG, and a hydrophilic polymer, e.g. PVA, without prior treatment or formation of an undercoat layer. To form a coated balloon, a PVA modified balloon or unmodified balloon can then be coated with a therapeutic coating solution. In some embodiments, the solution has a phenolic compound/hydrophilic polymer ratio (PC/HP) from about 10/90 to about 90/10, in other embodiments, from a ratio of about 20/80 to about 80/20, in additional embodiments, from a ratio of about 30/70 to about 70/30. A person of ordinary skill in the art will recognize that additional ratio ranges within the explicit ranges above are contemplated and are within the present disclosure. The coating solution in general comprises about 0.1% by weight to about 30% by weight of the phenolic compound and the hydrophilic polymer combined, in some embodiment, about 0.5% to about 20%, in additional embodiment about 1% to about 15%. A person of ordinary skill in the art will recognize that additional percentage concentration ranges within the explicit ranges above are contemplated and are within the present disclosure.

In some embodiments, before the coating process, the balloon is inflated to its nominal dimension. The inflated balloon is then submersed in the coating solution for a sufficient period of time, for example, up to 10 seconds after which time the balloon is withdrawn from the coating solution at a constant rate. The coated balloon is then placed in a convection oven for a sufficient period of time and allowed to dry, for example, the heating can be performed at 50° C. for about 30 minutes. In some embodiment, vacuum may be applied simultaneously to facilitate the drying process. After the drying process, the coated balloon formed with isocyanate linkage can be tested to determine the presence of any residual isocyanate groups. In one embodiment the coated balloon before or after drying can be further treated with a capping agent such as ethanol to cap the unreacted isocyanate groups on the balloon surface. In some embodiments, an additional sacrificial coating such as sugar can be coated on the coated balloon to provide protection of the PGG in the balloon coating. In general, at least 5% by weight of the coating of the coated balloon comprises a phenolic compound such as PGG, in another embodiment, at least 25% by weight, in additional embodiment, at least 50% by weight, in some embodiment, at least 70% by weight, in still further embodiment, at least 90% by weight. A person of ordinary skill in the art will recognize that additional percentage ranges within the explicit ranges above are contemplated and are within the present disclosure.

Treatment Procedure Using the Coated Balloon Device

The coated balloon is designed for delivery of therapeutic agents directly to a diseased portion of a blood vessel. The diseased portion of the vessel can be identified, for example, using appropriate imaging techniques, such as ultrasound, x-rays with contrast dye, magnetic resonance imaging, CAT scans or the like. The use of magnetic resonance and CT imaging techniques to guide procedures on aneurysms is described further in U.S. Pat. No. 6,463,317 to Kucharczyk et al., entitled "Device and Method for the Endovascular Treatment of Aneurysms," and U.S. Pat. No. 6,793,664 to Mazzocchi et al., entitled "System and Method of Minimally-Invasive Exovascular Aneurysm Treatment," both of which are incorporated herein by reference. Other vascular diseases, such as vulnerable plaque or an aortic dissection, can be correspondingly diagnosed to identify the treatment location. The diagnosis and treatment of vulnerable plaque using elastin stabilization compositions is described further in published U.S. patent application 2011/0218517 to Ogle et al., entitled "In Vivo Chemical Stabilization of Vulnerable Plaque," incorporated herein by reference. Treatment of aortic dissection and related pathologies is described further in copending U.S. patent application Ser. No. 13/362,492 to Ogle et al., entitled "Devices, Therapeutic Compositions and Corresponding Percutaneous Treatment Methods for Aortic Dissection," incorporated herein by reference. A procedure for delivery of a coated balloon as described herein at the location of an aneurysm is described in the following paragraphs. The corresponding procedures for the delivery of the coated balloon at locations of other pathologies follows similar procedures with appropriate access into the blood vessels based on the particular location of the pathology.

Figure 8:
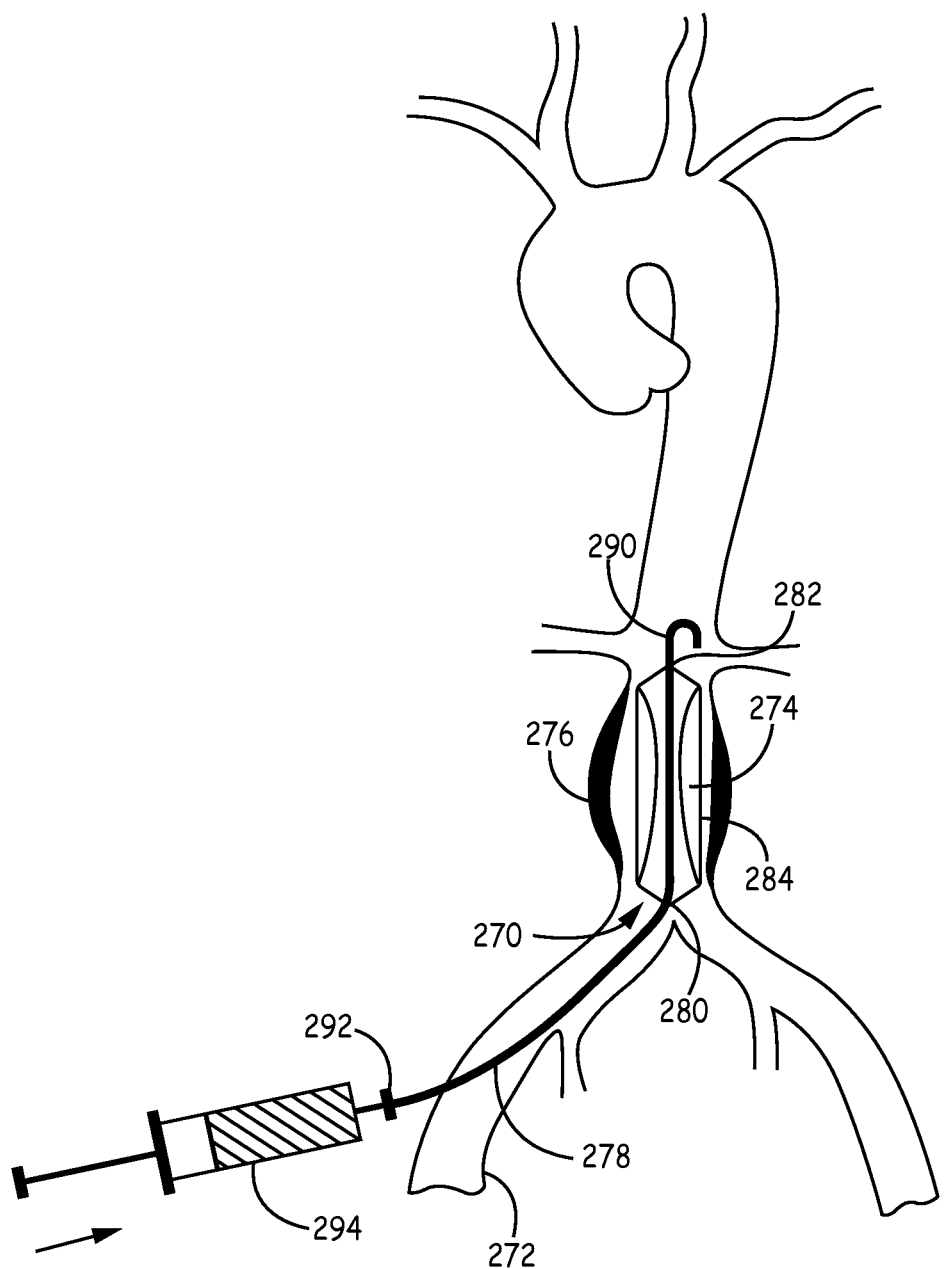
FIG. 8 is a front view with exposed blood vessels depicting a coated balloon supported on a balloon catheter positioned with the balloon at an abdominal aortic aneurysm.

The coated balloon device described herein can be tested in a model of abdominal aorta aneurysm, which is a good mimic of the human anatomy, providing a fairly realistic feel for the deployment of endovascular devices in the actual vasculature. The following steps were performed with the coated balloon device: (1). Insert the device into the model femoral artery in the model. (2). Guide the coated balloon of the device to the aneurysm. (3). Deploy the coated balloon to make good contact with the wall of the aneurysm. (4). Keep the deployed coated balloon at aneurysm for a sufficient period of time to allow delivery of the therapeutic compositions such as PGG. (5). Transform the deployed coated balloon to a low profile configuration and remove the device from the model femoral artery. FIG. 8 shows the coated balloon deployed in the abdominal aorta aneurysm model, compliant with the vessel wall. During the delivery and treatment process, the following characteristics of the procedure can be evaluated: (1) Ease of deployment, guidance of the coated balloon to appropriate area of aorta, and deployment of balloon. (2). Delivery, the aneurysm stabilizing agent should be able to be easily eluted or diffused through the device without the detachment of the coating and/or formation of particles. (3). Ease of removal, although no problems are foreseen, the device should be able to be easily removed from the model, allowing for restoration of normal fluid (blood) flow after the treatment procedure.

Figure 7A:
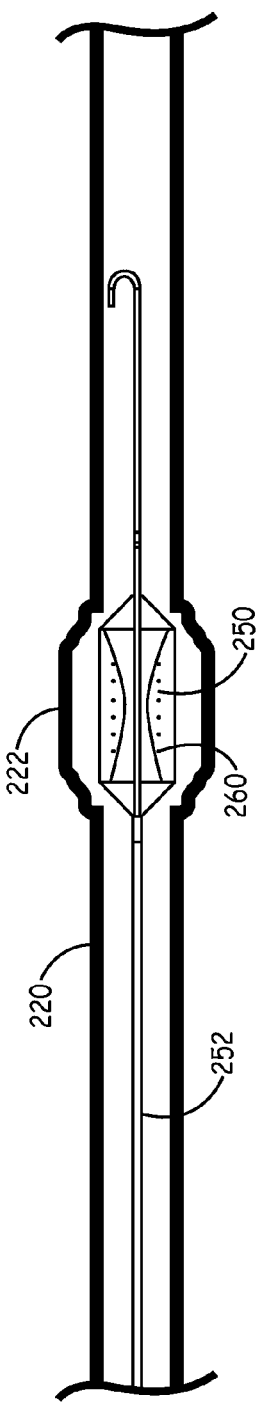
FIG. 7A shows an unextended coated balloon delivered to the aneurysm of a blood vessel.
Figure 7B:
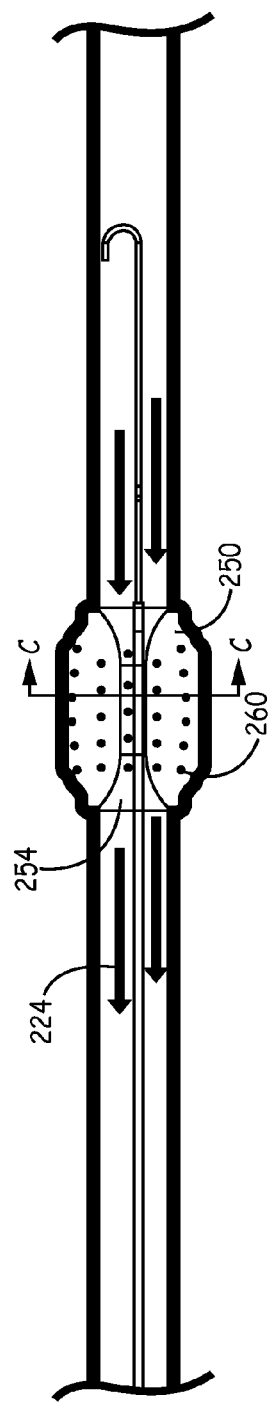
FIG. 7B shows the balloon of FIG. 7A in an extended configuration contacting the wall of the aneurysm of the blood vessel.
Figure 7C:
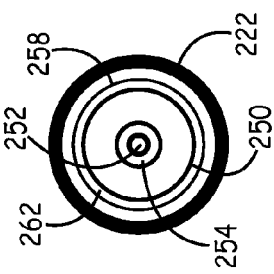
FIG. 7C shows the cross sectional view of the deployed balloon in the aneurysm along the C-C line of FIG. 7B.

Referring to FIGS. 7A-7C, a process of deploying the coated balloon device 250 is shown at a section of blood vessel 220 that has aneurysm 222. The procedure is described in the context of one embodiment of the coated balloon, and similar procedures can follow for other embodiments. As shown in FIG. 7A, a coated balloon device 250 is delivered with a guide catheter 252 to position the balloon at the location of the aneurysm 222. FIG. 7B shows when the balloon 250 is deployed at the aneurysm, the compliant balloon is inflated to make contact between the balloon coating 258 and the aneurysm 222. The coated balloon 250 comprises a by-pass channel 254 to allow blood flow 224 to pass through during the treatment process. FIG. 7C is a cross sectional view of FIG. 7B along the C-C line, showing the coating 258 and undercoat layer 262 on the balloon surface 250 has become hydrated and swollen and is in close contact with aneurysm 222. In some embodiment, the undercoated layer 262 may be made porous as shown in FIG. 7C. Upon exposing the coated balloon to blood, the porous undercoat 262 can be hydrated quickly due to the presence of the pores. The hydrated undercoat then facilitates quick release of the elastin stabilization agent in the coating 258 into the surrounding blood vessel. The balloon 250 may be additionally made to have small pores 260 to allow fluid to weep through the balloon surface to further facilitate the delivery of the stabilization agent.

Figure 9:
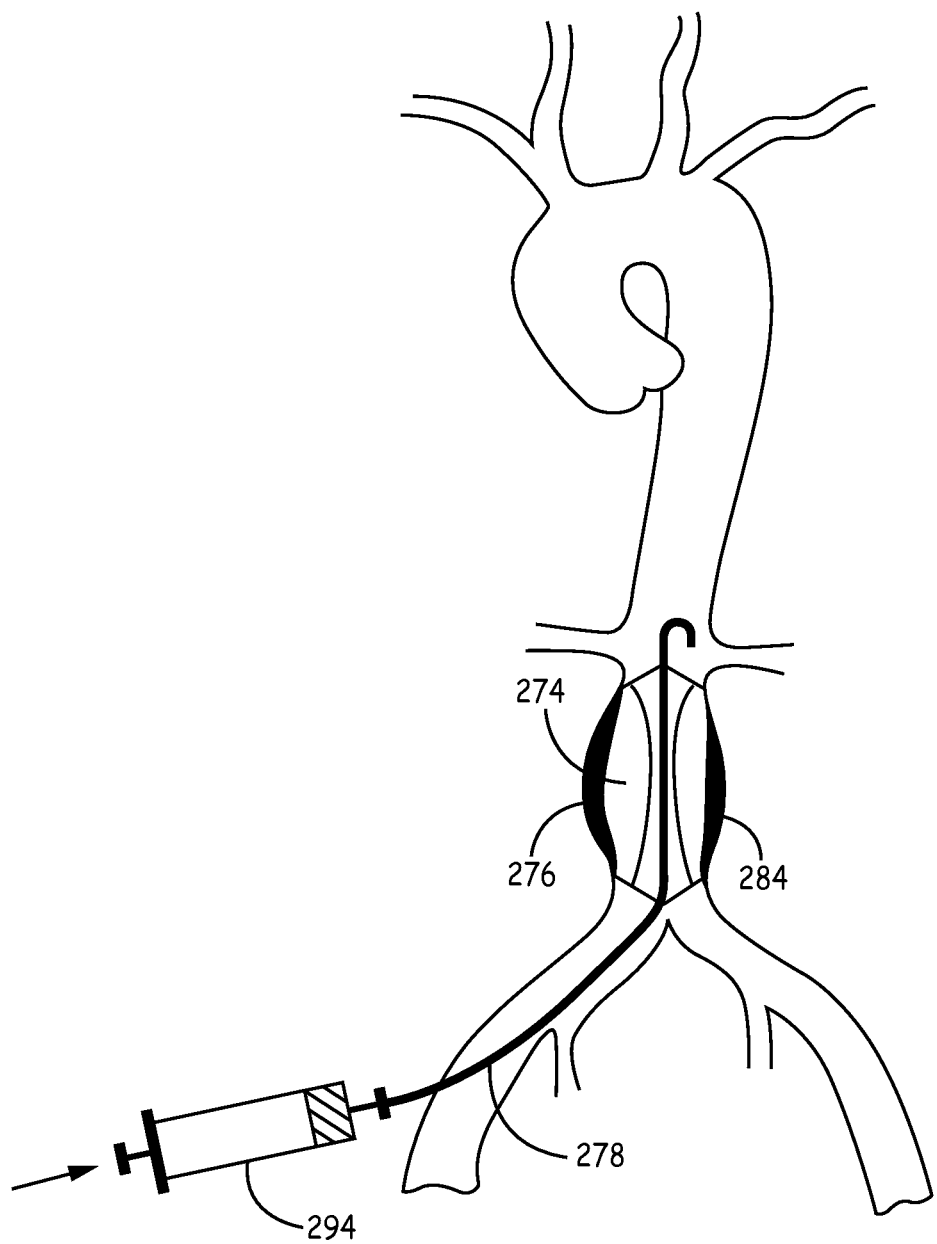
FIG. 9 is a front view of the device positioned as shown in FIG. 8 following deployment of the balloon.
Figure 10:
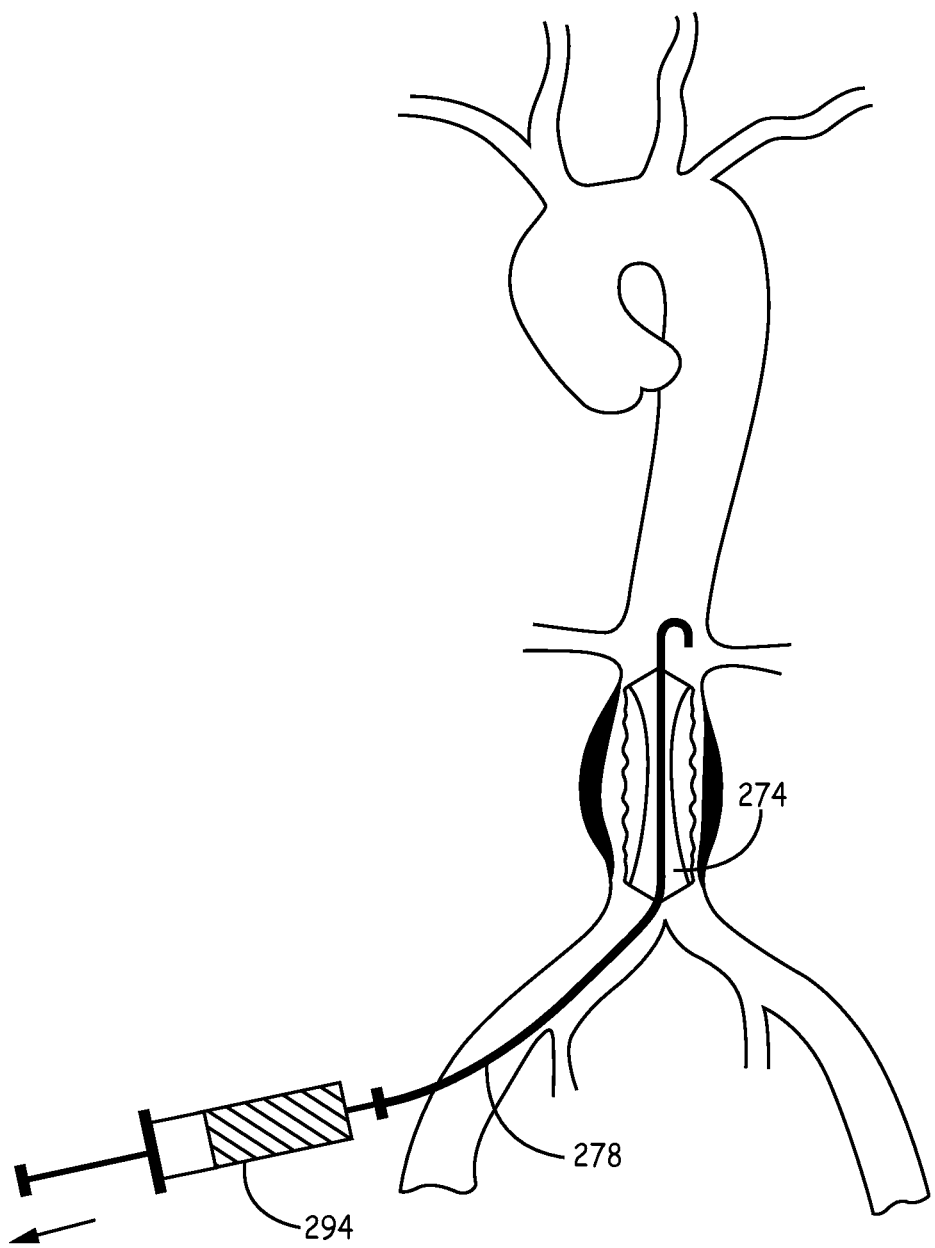
FIG. 10 is a front view of the device positioned as shown in FIG. 8 following deflation of the balloon.

As shown in FIGS. 8-10, the device can be used for the delivery of a therapeutic composition at an aortic aneurysm. As shown in FIG. 8, the coated balloon device 270 is introduced into the vasculature at a femoral artery 272. Device 270 is tracked up femoral artery 272 to place balloon 274 in position at an aortic aneurysm 276 with balloon catheter 278 extending from the balloon to the exterior of the patient. Radiopaque markers 280, 282 can be placed on the coated balloon device 270 to facilitate placement of the device by visualization using x-ray during delivery. Balloon 274 further comprises a coating 284. The coated balloon may optionally have a sheath to protect the coating 284 of the coated balloon during delivery, as described further below in the context of FIG. 11. Balloon catheter 278 comprises a distal guidewire 290 extending from the distal end of balloon catheter 278 and a fitting, such as a Luer fitting 292 at the proximal end of the balloon catheter for attachment to a fluid delivery device, shown as a syringe 294. Fluid can be delivered to expand the balloon by pushing the syringe to deliver fluid to the balloon and removed from the balloon by pulling the syringe to deflate the balloon for removal. As shown in FIG. 9, once balloon 274 is inflated, coating 284 of the compliant balloon forms a contact with the aneurysm 276.

After the polyphenolic compounds have been sufficiently delivered into the aneurysm, the syringe 294 is used to withdraw fluid from the balloon to collapse the balloon. As shown in FIG. 10, balloon 274 can be deflated following delivery of the therapeutic composition from the coating into the vessel wall. FIG. 10 shows the collapsed balloon that is ready to be removed. After the deflation of balloon 274, coated balloon device 270 can be removed from the patient. The treatment of other vessel pathologies follows similarly to the procedure outlined in FIGS. 8-10 with proper location and delivery of the balloon.

Figure 11:
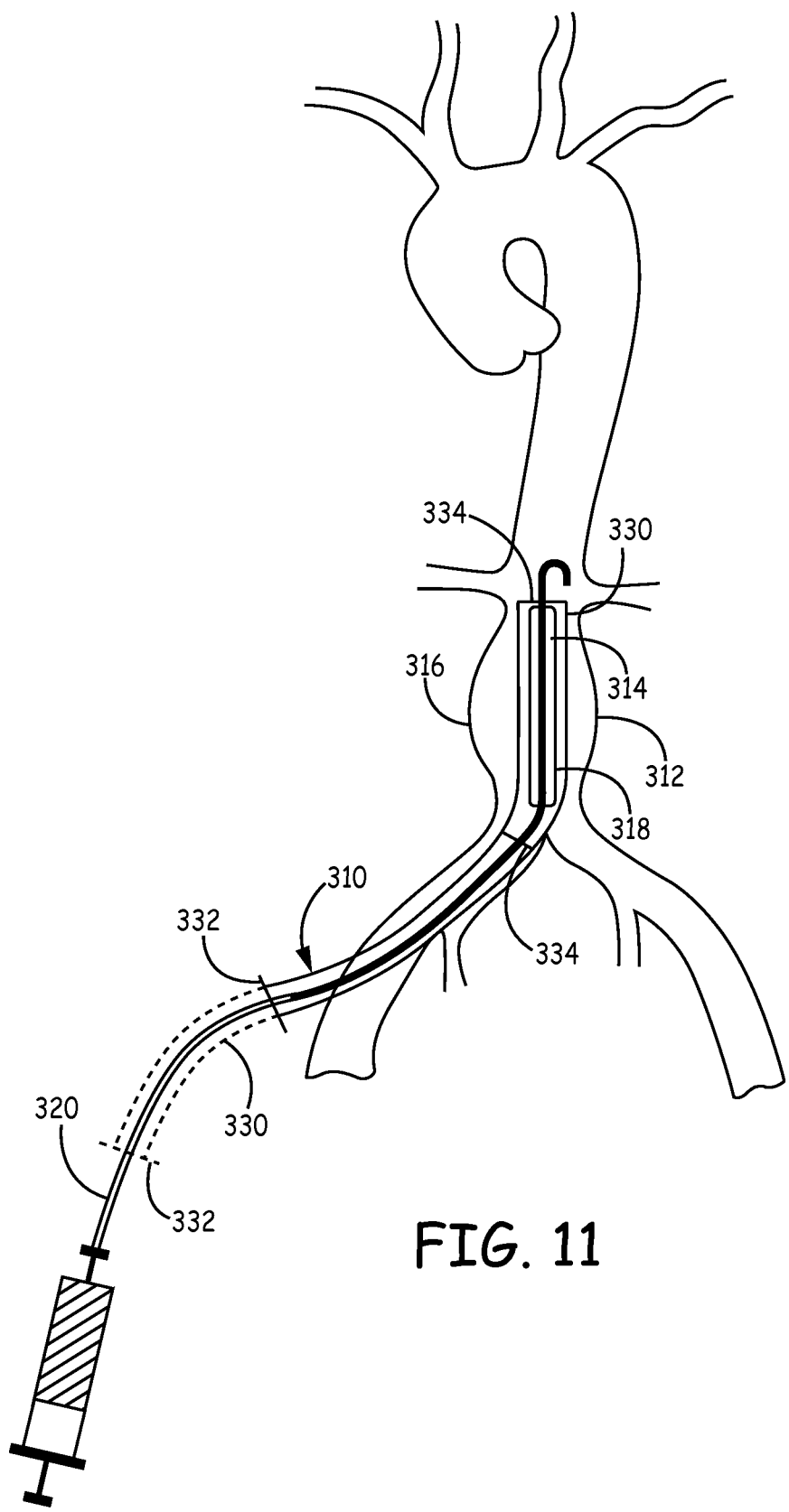
FIG. 11 is a front view of a coated balloon device positioned at an aortic aneurysm with a sheath covering the balloon.

As noted above, the coated balloon can be delivered with the assistance of a sheath that is used to cover the balloon while it is being placed in position. The sheath can reduce or eliminate contact of the balloon surface with the patient's blood until the sheath is withdrawn by the medical professional performing the procedure. An embodiment of a balloon with a sheath cover is shown in FIG. 11. Medical device 310 is shown in position in the aorta 312 with a balloon 314 at the location of an aneurysm 316. Balloon 314 has a coating 318 and is connected to a balloon catheter 320. A sheath 330 covers the balloon 314. Sheath 330 has a tubular structure that extends over balloon catheter 320 to location exterior to the patient. As shown in FIG. 11, sheath 330 has a handle 332 near its proximal end. Handle 332 can be manually engaged, or a tool can be attached to the handle to facilitate movement of the handle. When balloon 314 is in position, sheath 330 can be withdrawn to expose the balloon, as shown in phantom lines in FIG. 11. Distal end 334 of sheath 330 can be placed away from balloon 314 so that the sheath does not interfere with deployment of the balloon. Once sheath 330 is withdrawn, deployment and removal of the balloon can follow as shown in FIGS. 9 and 10.

The contact between the coating of the inflated coated balloon and the vessel wall is maintained for a sufficient period of time to allow sufficient delivery of the polyphenolic compounds into the vessel wall at the location of the vessel pathology. Depending on the location, the patient may or may not tolerate extended period of flow stoppage in the vessel. For example, in the aorta below the renal arteries, a patient can generally tolerate moderate period of flow stoppage, such as on the order of 30 minutes. If the desired delivery time is longer than the safe period to stop flow, a device with a bypass channel can be used. In some embodiments, the contact with the inflated balloon and the vessel wall can be maintained for about 30 seconds to about 60 min, in other embodiment, for about 2 min to about 30 min, in further embodiment, for about 3 min to about 20 min. A person of ordinary skill in the art will recognize that additional ranges of time within the explicit ranges above are contemplated and are within the present disclosure.

Sterilization and Packaging

The coated balloons described herein can be sterilized prior to and/or following packaging and subsequent distribution. The materials used in the balloon as well as the coating should be compatible with the sterilization process without changing the material properties in a detrimental way or removing the stabilization efficacy of the stabilization composition. In particular, the sterilization technique and materials can be selected so that a significant amount of crosslinking does not result during the sterilization process. The sterilization process should be compatible with the balloon and associated therapeutic compositions without causing crosslinking or interactions between the components or compositions in the balloon coating. Sterilization methods disclosed for example in U.S. Pat. No. 7,794,775 to Stratford et al. entitled "Balloon Expandable Stent", U.S. Pat. No. 7,695,674 to Varma et al. entitled "Method of Sterilizing Balloon with Ionizing Radiation", U.S. Pat. No. 7,150,853 to Lee et al. entitled: "Method of Sterilizing a Medical Device", and U.S. Pat. No. 6,986,868 to Madsen entitled: "Method of Sterilizing a Medical Device Having a Hydrophilic Coating", all incorporated herein by reference, can be adopted for use to sterilize the devices described herein.

The device in a sterile container, such as a sealed plastic bag, can be distributed for use. The bag can then be opened in a relatively sterile procedure room for use. The device generally is distributed with appropriate instructions for use, which generally have received approval from the appropriate regulatory agency.

EXAMPLES

Example 1 Modification of the Surface of the Balloon

In general, the balloons used for testing were obtained from commercial sources such as Vention/Advanced Polymer that has a diameter of 20-35 mm, a length of 50 mm, and a material of very low durometer urethane. The balloon assemblies with the delivery catheter etc. were built in house or through an outside original equipment manufacturer such as Cartika. In general, during the treatment process, the balloon was inflated to its nominal dimension. The surface of the balloon was treated with an aliphatic diisocyanate such as hexamethylene diisocyanate in a volatile solvent so one of the isocyanate groups bind to the urethane linkages on the balloon surface, leaving the other isocyanate group available for further reaction. The diisocyanate treated balloon was then reacted with a solution of polyvinyl alcohol (PVA) in water and isopropyl alcohol (IPA) mixture to bind the PVA to the available isocyanate group on the surface of the balloon. Alternatively, instead of water and IPA, methyl ethyl ketone (MEK) has been reported by Sahatjian et al. in U.S. Pat. No. 5,304,121 as a solvent to make the solution of PVA. The balloon surface was thus modified with PVA via a diisocyanate linkage. The PVA modified balloon was then dried in an oven for example at 85° C. for 30 min.

Example 2 Formation of the Coated Balloon

In general, before the coating process, the balloon was inflated to its nominal dimension. In some embodiments, a balloon may be coated directly with a coating solution such as a PGG/PVA solution without prior treatment or formation of an undercoat layer. Alternatively, the PVA modified balloon from example 1 was coated with the PGG/PVA solution. The PGG/PVA solution in general has a PGG/PVA ratio of 50/50 in water and isopropyl alcohol (IPA) mixture. For example, the coating solution can comprise 2-4 wt % PVA, 1-3 wt % PGG, 30-40 wt % IPA, with remainder comprise DI water.

The inflated balloon was then submersed in the PGG/PVA coating solution for 10 seconds after which time the balloon was withdrawn from the coating solution at a constant rate. The PGG coated balloon was then dried under vacuum at 50° C. overnight to form the coated balloon. For balloons that were pretreated as outlined in Example 1, the coated balloon was also tested to determine the presence of any residual isocyanate groups. In one embodiment the coated balloon before or after drying can be further treated with a capping agent with hydroxyl groups or compounds containing primary or secondary amine groups such as methyl or ethyl alcohol, ethyl amine, ethanolamine, diethanolamine to cap the unreacted isocyanate groups on the balloon surface. In some embodiments, an additional sacrificial coating such as sugar can be coated on the coated balloon to provide protection of the PGG in the balloon coating. In general, the coated balloon can be sterilized using for example e-beam sterilization.

Example 3 Evaluate Coated Balloon in an Aortic Model

Testing of the coated balloon device from example 2 that does not contain the undercoat layer was performed with the assistance of a model of abdominal aorta aneurysm, which is a good mimic of the human anatomy. These models were made in house and by Elastrat, providing a fairly realistic feel for the deployment of endovascular devices in the actual vasculature. The following steps were performed with the coated balloon device of Example 2: (1). Insert the device into the model femoral artery in the model. (2). Guide the coated balloon of the device to the aneurysm. (3). Deploy the coated balloon to make good contact with the wall of the aneurysm. (4). Keep the deployed coated balloon at aneurysm for a sufficient period of time to allow delivery of the therapeutic compositions such as PGG. (5). Transform the deployed coated balloon to a low profile configuration and remove the device from the model femoral artery. FIG. 8 shows the coated balloon deployed in the abdominal aorta aneurysm model, compliant with the vessel wall.

The following characteristics of the procedure can be evaluated: (1) Ease of deployment, guidance of the coated balloon to appropriate area of aorta, and deployment of balloon. (2). Delivery, the aneurysm stabilizing agent should be able to be easily eluted or diffused through the device without the detachment of the coating and/or formation of particles. (3). Ease of removal, although no problems are foreseen, the device should be able to be easily removed from the model, allowing for restoration of normal fluid (blood) flow after the treatment procedure.

Alternatively, testing of the coated balloon device from example 2 with or without the undercoat layer can be performed with the assistance of a vascular model to mimic human anatomy with a section at the location of the infrarenal abdominal aorta where segment of porcine or human cadaver tissue can be connected. The model can use a fresh abdominal aorta from a porcine, a healthy abdominal aorta from cadaver, or a diseased abdominal aorta from a cadaver. The steps outlined above can be performed followed by evaluation of the treated tissue via mechanical testing to measure increase in mechanical strength and modulus of the tissue. Alternatively or additionally, the treated tissue can also be evaluated by enzymatic degradation testing to protective properties of the PGG against enzymatic degradation. For example, testing procedures outlined in U.S. Pat. No. 7,252,934, incorporated herein by reference can be adapted and used, The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A coated balloon device for stabilizing a section of a blood vessel in a living subject comprising,
a shaft having a proximal end and a distal end, a balloon element comprising an extendable structure having an outer surface, the balloon element being supported by the shaft at or near the distal end of the shaft, wherein the extendable structure of the balloon element comprises a compliant polymer, a coating layer associated with the outer surface of the extendable structure, and a hydrophilic undercoat layer between the balloon element and the coating layer, wherein at least 5% by weight of the coating layer comprises a therapeutic composition that comprises a phenolic composition comprising tannic acid or an analog of tannic acid, pentagalloylglucose or an analog of pentagalloylglucose, a combination thereof, or a pharmaceutically acceptable salt thereof, and wherein the extendable structure of the balloon element comprises an unextended configuration, an inflated but un-expanded configuration and an expanded configuration.

2. The coated balloon device of claim 1 wherein the therapeutic composition has little or no unbound gallic acid.

3. The coated balloon device of claim 1 wherein the phenolic compound comprises pentagalloylglucose.

4. The coated balloon device of claim 1 wherein at least 50% by weight of the coating layer comprises the phenolic compound.

5. The coated balloon device of claim 1 wherein the coating layer have a thickness from about 20 microns to about 50 microns.

6. The coated balloon device of claim 1 wherein the therapeutic composition further comprises glutaraldehyde.

7. The coated balloon device of claim 1 wherein the coating layer further comprises a hydrophilic polymer.

8. The coated balloon device of claim 7 wherein the hydrophilic polymer comprises polyvinyl alcohol, polyvinyl pyrrolidone, polyethylene glycol, poly(lactic-co-glycolic acid), or a combination thereof.

9. The coated balloon device of claim 7 wherein the hydrophilic polymer comprises polysaccharide, dextran, starch, hyaluronic acid, collagen, gelatin, chitin, albumin, alginate, as such or as a derivative or a combination thereof.

10. The coated balloon device of claim 1 wherein the inflated but unexpanded configuration has a generally cylindrical section along the outer surface.

11. The coated balloon device of claim 1 wherein the extendable structure of the balloon element is a low durometer polyurethane balloon material.

12. The coated balloon device of claim 1 wherein the shaft comprises a balloon lumen having a distal opening into the interior of the balloon element and a proximal connection connected to a fluid source.

13. The coated balloon device of claim 1 further comprising a by-pass channel with an opening proximal to the balloon element and an opening distal to the balloon element that provides flow past the balloon when expanded in a vessel.

14. The coated balloon device of claim 1 wherein the undercoat layer has a thickness of from about 5 micron to about 50 microns.

15. The coated balloon device of claim 1 wherein the thickness ratio between the coating layer and the undercoat layer is from about 1:1, to about 10:1.

16. The coated balloon device of claim 1 wherein the undercoat layer is crosslinked to the balloon element.

17. The coated balloon device of claim 1 wherein the undercoat layer is porous to allow further hydration of the coating layer.

18. The coated balloon device of claim 1 further comprising a sheath slidably positioned over the shaft having a configuration extended in a distal direction relative to the shaft covering the extendable structure in the unextended configuration.

19. The coated balloon device of claim 1 further comprising a sacrificial top coating that dissolves upon delivery into the section of the blood vessel and comprises a hydrophilic composition.

20. The coated balloon device of claim 19 wherein the hydrophilic composition of the top coating is sugar, sugar derivatives, or a combination thereof.

21. The coated balloon device of claim 19 wherein the top coating has a thickness of from about 5 micron to about 50 microns.

22. The coated balloon device of claim 19 wherein the thickness ratio between the undercoat layer, the coating layer, and the top coating is from about 30:40:30 to about 10:85:5.

23. A coated balloon device for stabilizing a section of a blood vessel in a living subject comprising, a shaft having a distal end and a proximal end, a balloon element comprising an extendable structure having an outer surface, the balloon element being supported by the shaft at or near the distal end of the shaft, wherein the extendable structure comprise a compliant polymer, a coating associated with the outer surface of the extendable structure, and a hydrophilic undercoat layer between the balloon element and the coating, wherein the coating comprises a hydrophilic polymer binder and a therapeutic composition blended with the hydrophilic polymer, the therapeutic composition comprising a phenolic composition comprising tannic acid or an analog of tannic acid, pentagalloylglucose or an analog of pentagalloylglucose, a combination thereof, or a pharmaceutically acceptable salt thereof.

24. The coated balloon of claim 23 wherein the hydrophilic polymer comprises polyvinyl alcohol, polyvinyl pyrrolidone, polyethylene glycol, poly(lactic-co-glycolic acid), or a combination thereof.

25. The coated balloon device of claim 23 wherein the hydrophilic polymer comprises polysaccharide, dextran, starch, hyaluronic acid, collagen, gelatin, chitin, albumin, alginate, as such or as a derivative or a combination thereof.

26. The coated balloon of claim 23 wherein the phenolic composition is pentagalloylglucose.

27. The coated balloon of claim 23 wherein at least 25% by weight of the coating comprises the phenolic compound.

28. The coated balloon of claim 23 wherein the coating layer have a thickness from about 20 microns to about 50 microns.

29. The coated balloon of claim 23 wherein the therapeutic composition further comprises glutaraldehyde.

30. The coated balloon of claim 23 further comprising a by-pass channel with an opening proximal to the balloon element and an opening distal to the balloon element that provides flow past the balloon when expanded in a vessel.

* * * * *